United States Patent
Montalvo et al.

(10) Patent No.: US 10,835,727 B2
(45) Date of Patent: Nov. 17, 2020

(54) THERAPEUTIC AGENT INJECTION DEVICE

(71) Applicant: Medtronic MiniMed, Inc., Northridge, CA (US)

(72) Inventors: Susan McConnell Montalvo, Woodland Hills, CA (US); Colin A. Chong, Glendale, CA (US); Hans Lickliter, Canyon Country, CA (US); Rafael Bikovsky, Oak Park, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 42 days.

(21) Appl. No.: 15/993,289

(22) Filed: May 30, 2018

(65) Prior Publication Data

US 2018/0272115 A1    Sep. 27, 2018

Related U.S. Application Data

(63) Continuation of application No. 15/167,485, filed on May 27, 2016, now Pat. No. 9,987,476, which is a
(Continued)

(51) Int. Cl.
*A61M 39/02* (2006.01)
*A61M 5/50* (2006.01)
(Continued)

(52) U.S. Cl.
CPC ........ *A61M 39/02* (2013.01); *A61M 5/14248* (2013.01); *A61M 5/158* (2013.01);
(Continued)

(58) Field of Classification Search
CPC ........ A61M 39/02; A61M 5/30; A61M 5/158; A61M 5/14248; A61M 5/5086;
(Continued)

(56) References Cited

U.S. PATENT DOCUMENTS 4,755,173 A    7/1988 Konopka et al.
4,781,688 A    11/1988 Thoma et al.
(Continued)

FOREIGN PATENT DOCUMENTS

CN    101128228 A    2/2008
EP    1403519 A1    3/2004
(Continued)

OTHER PUBLICATIONS

PCT International Search Report and Written Opinion for PCT/US2014/059864 dated Mar. 3, 2015.
(Continued)

*Primary Examiner* — Amber R Stiles
(74) *Attorney, Agent, or Firm* — Medtronic Minimed, Inc.

(57) ABSTRACT

A therapeutic agent injection device including an injection device for delivering a therapeutic agent to a patient having a body, the body having a patient face and a port face opposite the patient face, the port face having an introducer port including an introducer channel and an injection port including an injection channel, the introducer channel being in fluid communication with the injection channel through a cross channel, the injection channel defining an injection axis; a delivery tube for subcutaneous delivery of the therapeutic agent to the patient, the delivery tube projecting from and being generally perpendicular to the patient face, the delivery tube defining an introducer axis and being in fluid communication with the injection port; and a patch, the patch being attached to the patient face and being operable to adhesively attach to the patient; wherein the injection axis is parallel to the introducer axis.

15 Claims, 23 Drawing Sheets

Related U.S. Application Data continuation of application No. 14/491,716, filed on Sep. 19, 2014, now Pat. No. 9,375,537, which is a continuation-in-part of application No. 14/052,929, filed on Oct. 14, 2013, now Pat. No. 9,265,881.

(51) Int. Cl.
  *A61M 5/30* (2006.01)
  *A61M 5/158* (2006.01)
  *A61M 5/142* (2006.01)

(52) U.S. Cl.
  CPC ............ *A61M 5/30* (2013.01); *A61M 5/3007* (2013.01); *A61M 5/5086* (2013.01); *A61M 39/0208* (2013.01); *A61M 2005/3022* (2013.01); *A61M 2039/0205* (2013.01); *A61M 2039/0223* (2013.01); *A61M 2039/0226* (2013.01); *A61M 2205/18* (2013.01); *A61M 2205/3344* (2013.01); *A61M 2230/005* (2013.01); *A61M 2230/201* (2013.01)

(58) Field of Classification Search
  CPC ............ A61M 5/3007; A61M 39/0208; A61M 2039/0205; A61M 2039/0223; A61M 2039/0226; A61M 2205/3344; A61M 2230/005; A61M 2230/201; A61M 2005/3022; A61M 2205/18
  See application file for complete search history.

(56) References Cited

U.S. PATENT DOCUMENTS

| | | | |
|---|---|---|---|
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 9,987,476 B2 * | 6/2018 | Montalvo ......... A61M 39/0208 |
| 2004/0163716 A1 | 8/2004 | Madden et al. | |
| 2007/0123819 A1 | 5/2007 | Mernoe et al. | |
| 2007/0270748 A1 | 11/2007 | Dacquay et al. | |
| 2008/0215003 A1 * | 9/2008 | Kornerup .............. A61M 5/158 604/116 |
| 2008/0281297 A1 | 11/2008 | Pesach et al. | |
| 2010/0160861 A1 | 6/2010 | Causey, III et al. | |
| 2011/0009823 A1 | 1/2011 | Chong et al. | |
| 2011/0144587 A1 | 6/2011 | Stone | |

FOREIGN PATENT DOCUMENTS

| | | |
|---|---|---|
| WO | 02068015 A2 | 9/2002 |
| WO | 02068015 A3 | 9/2002 |
| WO | 2004024211 A2 | 3/2004 |
| WO | 2004024211 A3 | 3/2004 |
| WO | 2006032692 A1 | 3/2006 |
| WO | 2006097111 A2 | 9/2006 |
| WO | 2006097111 A3 | 9/2006 |
| WO | 2006108809 A1 | 10/2006 |
| WO | 2007108987 A2 | 9/2007 |
| WO | 2007108987 A3 | 9/2007 |
| WO | 2008092782 A1 | 8/2008 |
| WO | 2008092959 A1 | 8/2008 |
| WO | 2011133823 A1 | 10/2011 |
| WO | 2013086463 A1 | 6/2013 |

OTHER PUBLICATIONS

PCT International Search Report and Written Opinion for PCT/US2014/069945 dated Mar. 6, 2015.
PCT International Search Report and Written Opinion for PCT/US2014/069957 dated Mar. 6, 2015.
Extended European Search Report dated Oct. 14, 2019 for EP Application No. 19185515.4-1122 (8 pages).

* cited by examiner

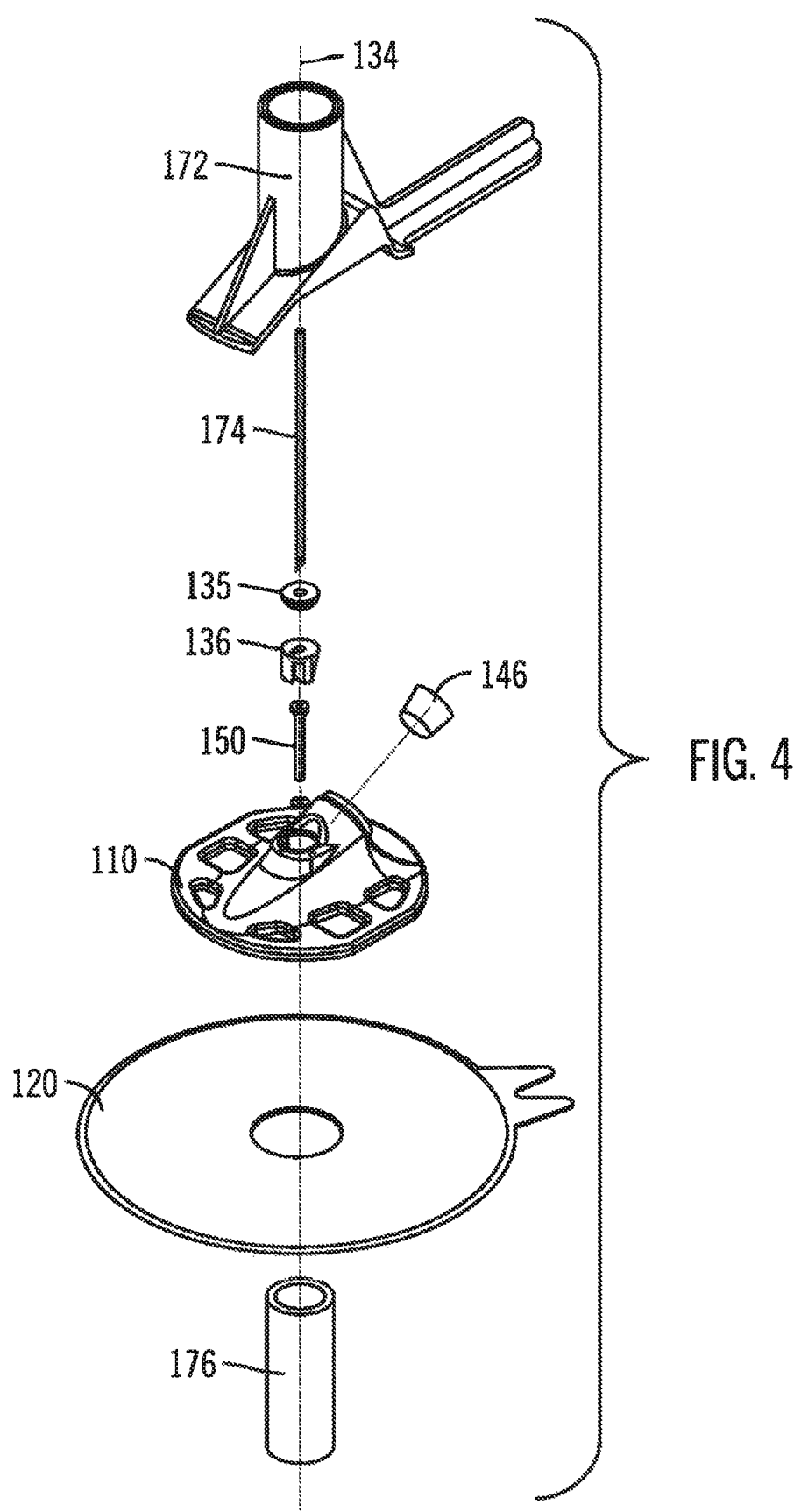

ated delivery of the therapeutic agent to the patient, the delivery
tube projecting from and being generally perpendicular to
the patient face, the delivery tube defining an introducer axis
and being in fluid communication with the injection port;
and a patch, the patch being attached to the patient face and
being operable to adhesively attach to the patient; wherein
the injection axis is parallel to the introducer axis.

THERAPEUTIC AGENT INJECTION DEVICE

CROSS-REFERENCE TO RELATED APPLICATIONS

This application is a continuation of U.S. patent application Ser. No. 15/167,485, filed on May 27, 2016, which is a continuation of U.S. patent application Ser. No. 14/491,716, filed on Sep. 19, 2014, now U.S. Pat. No. 9,375,537, which is a continuation-in-part of U.S. patent application Ser. No. 14/052,929, filed on Oct. 14, 2013, now U.S. Pat. No. 9,265,881, each of which is incorporated herein by reference.

TECHNICAL FIELD

The technical field of this disclosure is personal medical systems, particularly, therapeutic agent injection devices.

BACKGROUND OF THE INVENTION

Certain medical conditions or diseases require that patients intermittently inject a drug or therapeutic agent subcutaneously to maintain the medical condition or disease under control. Multiple daily injections (MDIs) may be required. One such medical condition is diabetes, for which insulin is injected to regulate blood glucose. An estimated twenty-six million people in the United States, or about 8% of the population, have diabetes. This percentage is expected to increase in the near-term as the population ages.

Certain patients are unlikely or unable to follow the drug regimen required to maintain their medical condition under control. Some patients are squeamish about injecting the drug themselves and others suffer adverse effects from repeated injections, such as bruising at the injection site. To accommodate such patients, injection ports have been developed which only require that the patient puncture their skin every few days to install an injection port, rather than injecting with a needle into their skin numerous times a day. Injection ports employ a cannula inserted subcutaneously, and the patient injects the drug into the injection port adhering to their skin rather than directly into their cutaneous tissue.

A new problem arises with damage to the injection port itself. When the injection needle strikes the injection port's cannula, the cannula may be damaged so that the delivery of the drug is no longer controlled. The drug leaks from the damaged portion of the cannula before reaching the required subcutaneous depth. Although a shorter injection needle can be used to attempt to avoid such problems, such needles may not be locally available, limit flexibility in requiring a certain needle length, and provide no assurance that the patient may not still use a longer needle that damages the injection port.

It would be desirable to have a therapeutic agent injection device that would overcome the above disadvantages.

SUMMARY OF THE INVENTION

One aspect of the invention provides an injection device for delivering a therapeutic agent to a patient, the injection device having a body, the body having a patient face and a port face opposite the patient face, the port face having an introducer port including an introducer channel and an injection port including an injection channel, the introducer channel being in fluid communication with the injection channel through a cross channel, the injection channel defining an injection axis; a delivery tube for subcutaneous delivery of the therapeutic agent to the patient, the delivery tube projecting from and being generally perpendicular to the patient face, the delivery tube defining an introducer axis and being in fluid communication with the injection port; and a patch, the patch being attached to the patient face and being operable to adhesively attach to the patient; wherein the injection axis is parallel to the introducer axis.

Another aspect of the invention provides an injection device for delivering a therapeutic agent to a patient, the injection device having a body, the body having a patient face and an port face opposite the patient face, the port face having an introducer port including an introducer channel and an injection port including an injection channel, the introducer channel being in fluid communication with the injection channel, the injection channel defining an injection axis; a delivery tube for subcutaneous delivery of the therapeutic agent to the patient, the delivery tube projecting from and being generally perpendicular to the patient face, the delivery tube defining an introducer axis and being in fluid communication with the injection port; and a patch, the patch being attached to the patient face and being operable to adhesively attach to the patient; wherein the body has a first body portion including the port face and a second body portion including the patient face, the first body portion and the second body portion being rotatably connected with a flange, the first body portion and the second body portion being independently rotatable about the introducer axis.

Another aspect of the invention provides an injection device for delivering a therapeutic agent to a patient, the injection device having a body, the body having a patient face and an port face opposite the patient face, the port face having an introducer port including an introducer channel and an injection port including an injection channel, the introducer channel being in fluid communication with the injection channel, the injection channel defining an injection axis; a delivery tube for subcutaneous delivery of the therapeutic agent to the patient, the delivery tube projecting from and being generally perpendicular to the patient face, the delivery tube defining an introducer axis and being in fluid communication with the injection port; a patch, the patch being attached to the patient face and being operable to adhesively attach to the patient; and a pop-up indicator disposed in the introducer channel, the pop-up indicator having a normal state when pressure in the introducer channel is normal and an alarm state when pressure in the introducer channel exceeds a predetermined value.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 1-4 are perspective, section, perspective, and exploded perspective views, respectively, of one embodiment of an injection device made in accordance with the invention.

DETAILED DESCRIPTION

FIGS. 1-5C, in which like elements share like reference numbers, are various views of one embodiment of an injection device made in accordance with the invention. The injection device includes an introducer port along an introducer axis and an injection port along an injection axis, with the injection axis being non-collinear with the introducer axis. In this embodiment, the injection axis is at an angle to and intersects with the introducer axis.

Figure 1:
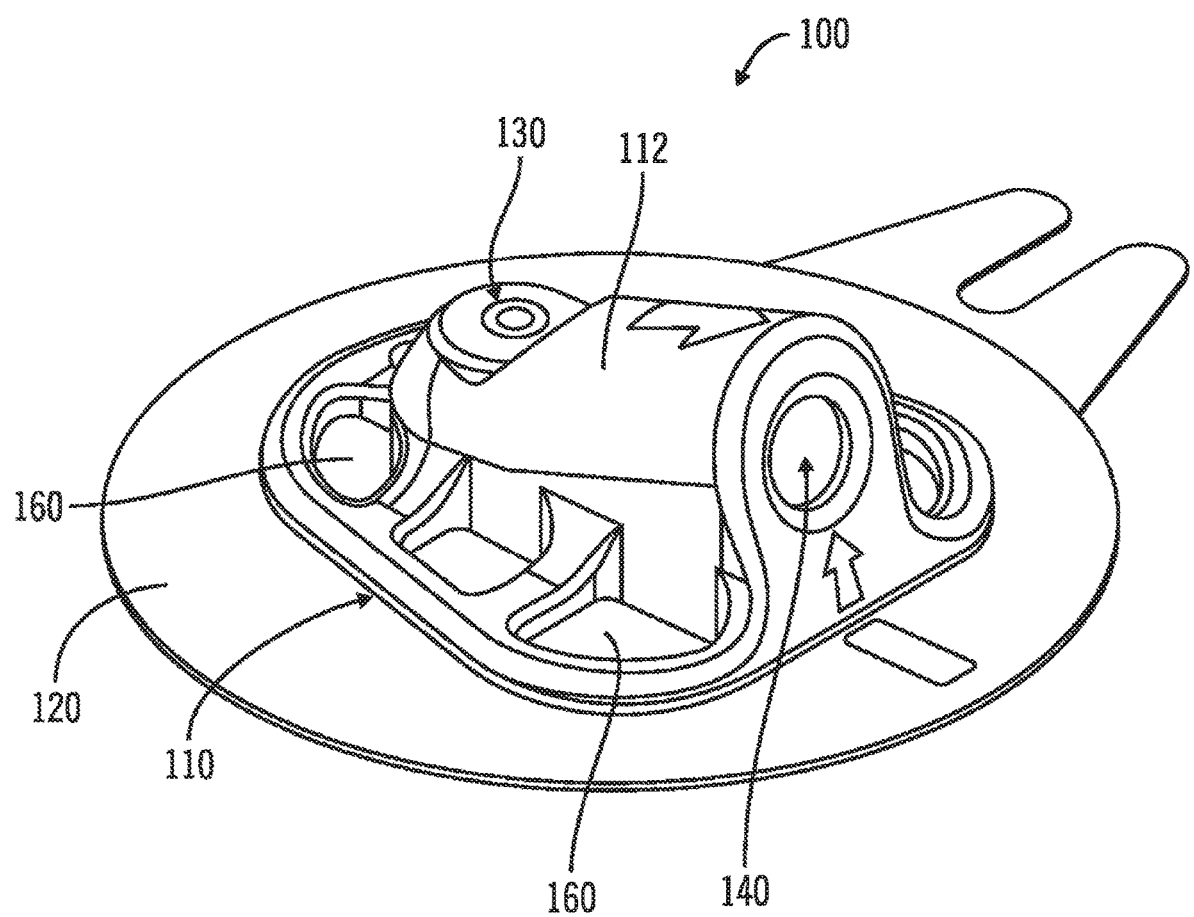

FIG. 1 is a perspective view of the injection device 100 including a body 110 and a patch 120 attached to the body 110. The patch 120 is operable to adhesively attach the injection device 100 to a patient (not shown). The body 110 has a port face 112, with an introducer port 130 and an injection port 140 on the port face 112. The introducer port 130 is used to place a delivery tube subcutaneously in the patient. The injection port 140 is used by the patient to inject a therapeutic agent, which as defined herein can be any liquid such as a liquid including a therapeutic agent, drug, diagnostic agent, or the like. The body 110 also includes cutouts 160. Those skilled in the art will appreciate that the introducer port 130 can be too small to be effectively used by a patient for injection, but could be used to inject a therapeutic agent, such as a bolus injection using a mechanically attached device, as desired for a particular application.

Figure 2:
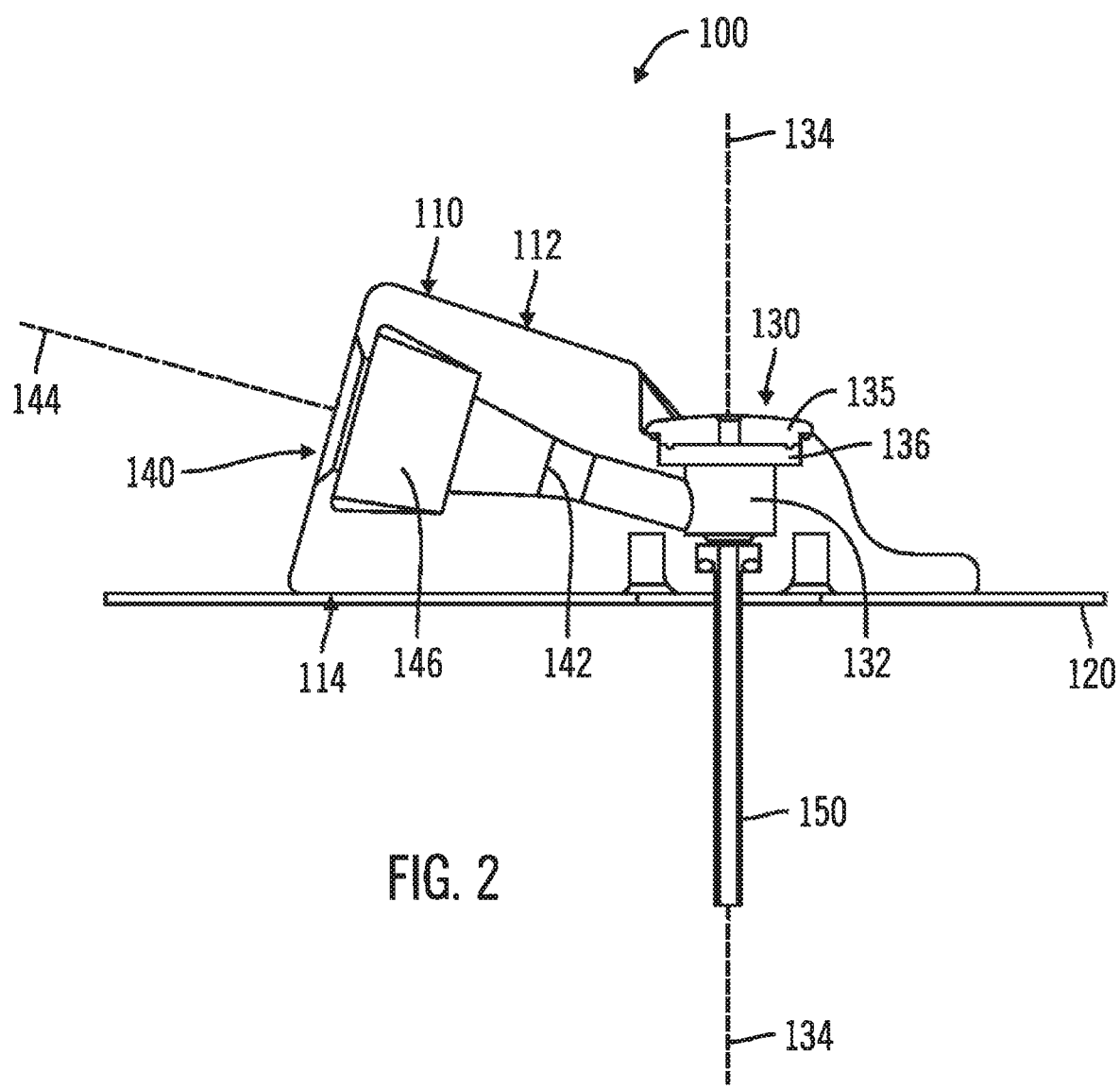

FIG. 2 is a section view of the injection device 100, the section bisecting the introducer port 130 and the injection port 140, and includes the introducer axis 134 and injection axis 144. An axis as defined herein generally follows the centerline of an associated channel through an associated port. The body 110 has a port face 112 and a patient face 114. A delivery tube 150 for subcutaneous delivery of the therapeutic agent projects from and is generally perpendicular to the patient face 114. The delivery tube 150 is operably connected to the introducer port 130 and defines an introducer axis 134 along the introducer channel 132, the delivery tube 150 being in fluid communication with the injection port 140. The introducer port 130 includes an introducer channel 132, with an introducer port cover 135 and an introducer septum 136 disposed in the introducer channel 132. The injection port 140 includes an injection channel 142 defining an injection axis 144 with an injection septum 146 disposed in the injection channel 142. In one embodiment, the introducer septum 136 and/or the injection septum 146 is self sealing, such that each of the septums block fluid flow through the septum after a needle has been put through the septum then removed, preventing fluid flow from the port. In this embodiment, the injection axis 144 is at an angle to and intersects with the introducer axis 134. In one example, the delivery tube 150 is a flexible cannula and a needle hub assembly can be used to place the delivery tube 150 subcutaneously in the patient. In another example, the delivery tube 150 is a rigid needle and the delivery tube 150 can be placed subcutaneously in the patient with or without a needle hub assembly.

Figure 3:
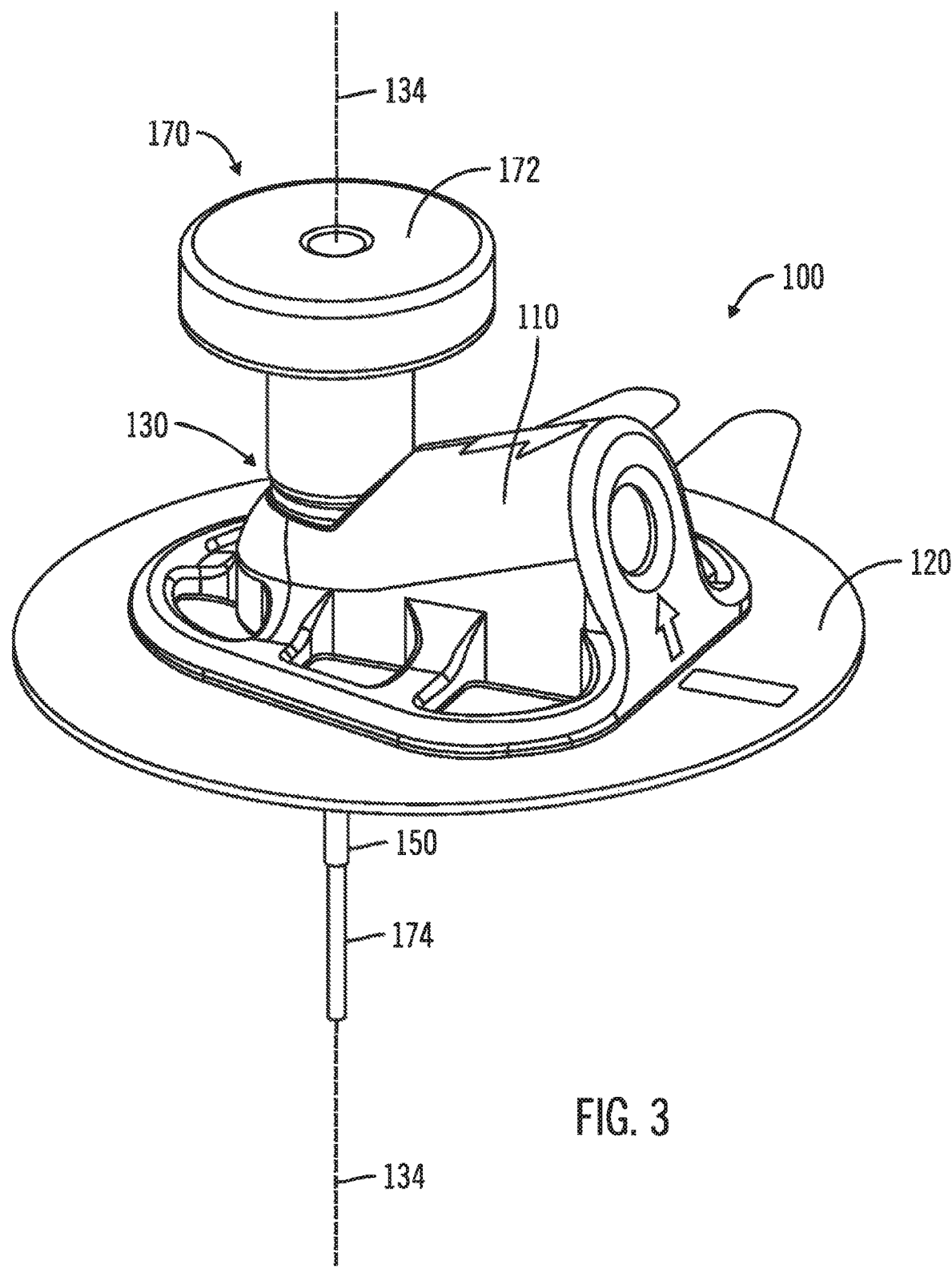

FIG. 3 is a perspective view of the injection device 100 with a needle hub assembly 170. The needle hub assembly 170 includes a needle hub 172 and a needle 174 attached to the needle hub 172. The needle 174 of the needle hub assembly 170 is inserted through the introducer port 130 and through the delivery tube 150 along the introducer axis 134. The needle hub assembly 170 can be used to add rigidity to the delivery tube 150 during implantation when the delivery tube 150 is a flexible cannula.

FIG. 4 is an exploded perspective view of the injection device with a needle hub assembly. A needle guard 176 disposed around the needle 174 can be used to protect the needle 174 and the delivery tube 150 when the injection device and needle hub assembly are assembled for shipping. The various parts of the injection device and needle hub assembly can be connected by interference fit, adhesive, welding, and/or any other method of attachment suitable for a particular application.

Figure 5A:
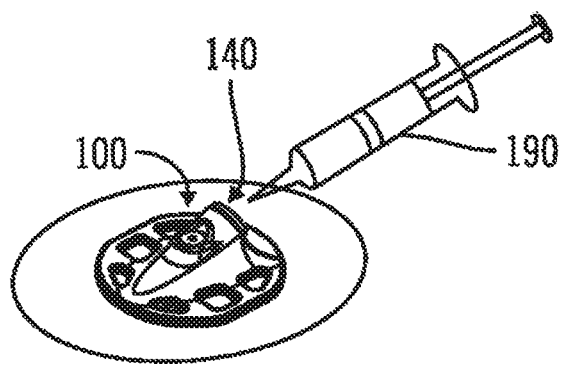
FIGS. 5A-5C are perspective views of one embodiment of an injection device made in accordance with the invention.
Figure 5B:
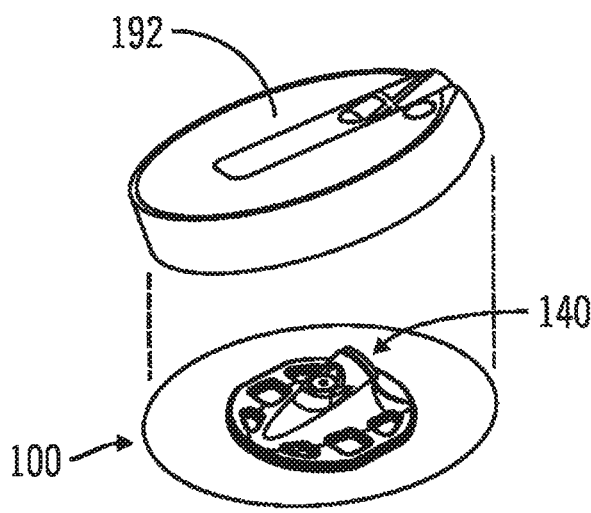
Figure 5C:
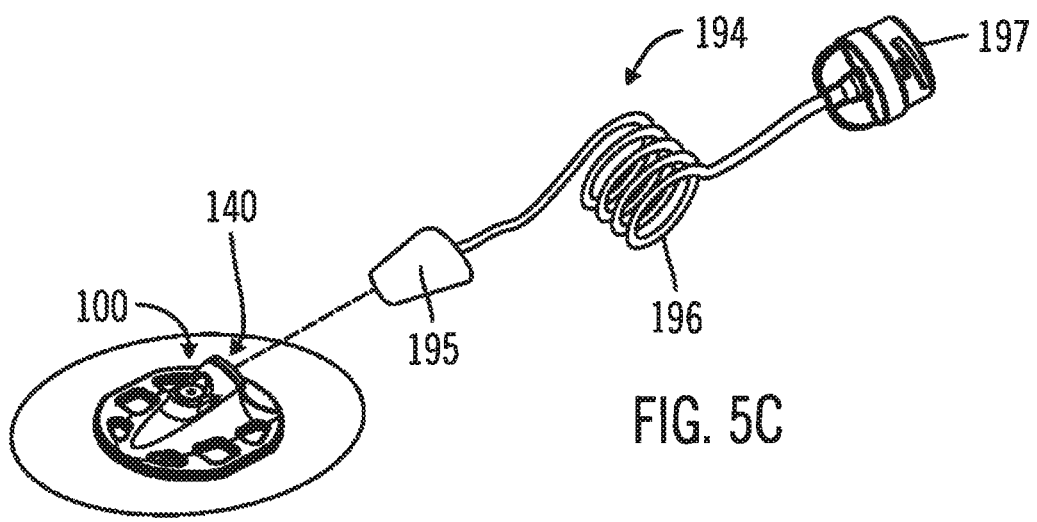

FIGS. 5A-5C are perspective views of various applications of the injection device made in accordance with the invention. Referring to FIG. 5A, a syringe 190 can be used to deliver a therapeutic agent through the injection port 140 of the injection device 100. The syringe can be a conventional syringe, a standard insulin pen, or a needleless syringe. The needle length of a conventional syringe or standard insulin pen can be of any length because the injection axis is non-collinear with the introducer axis, such that a longer needle does not damage the injection device. In one embodiment, the injection port 140 is adapted to be mateable with the syringe 190, with a socket, fitting, or the like, to increase ease of use. In one example, the injection port 140 is a socket with a socket needle which pierces a foil front end of a needleless syringe when the needleless syringe is seated in the socket. The needleless syringe itself has no needle in this example.

Referring to FIG. 5B, an on-body injector 192 is mateable with the injection port 140 of the injection device 100 and can be used to deliver a therapeutic agent through the injection port 140. The on-body injector 192 can include a reservoir to hold the therapeutic agent. In one embodiment, the on-body injector 192 can deliver a basal and/or bolus dose of the therapeutic agent.

Referring to FIG. 5C, an extendable tube 194 can be used to deliver a therapeutic agent through the injection port 140.

The extendable tube 194 includes a port connector 195, a tube 196, and an external device fitting 197, all being in fluid communication. The port connector 195 is in fluid communication with the injection port 140 with a needle or mateable fitting to deliver the therapeutic agent through the injection port 140. The external device fitting 197 is connectable to an external device, such as a wearable insulin pump or an infusion tubing line to a gravity fed container.

Figure 6:
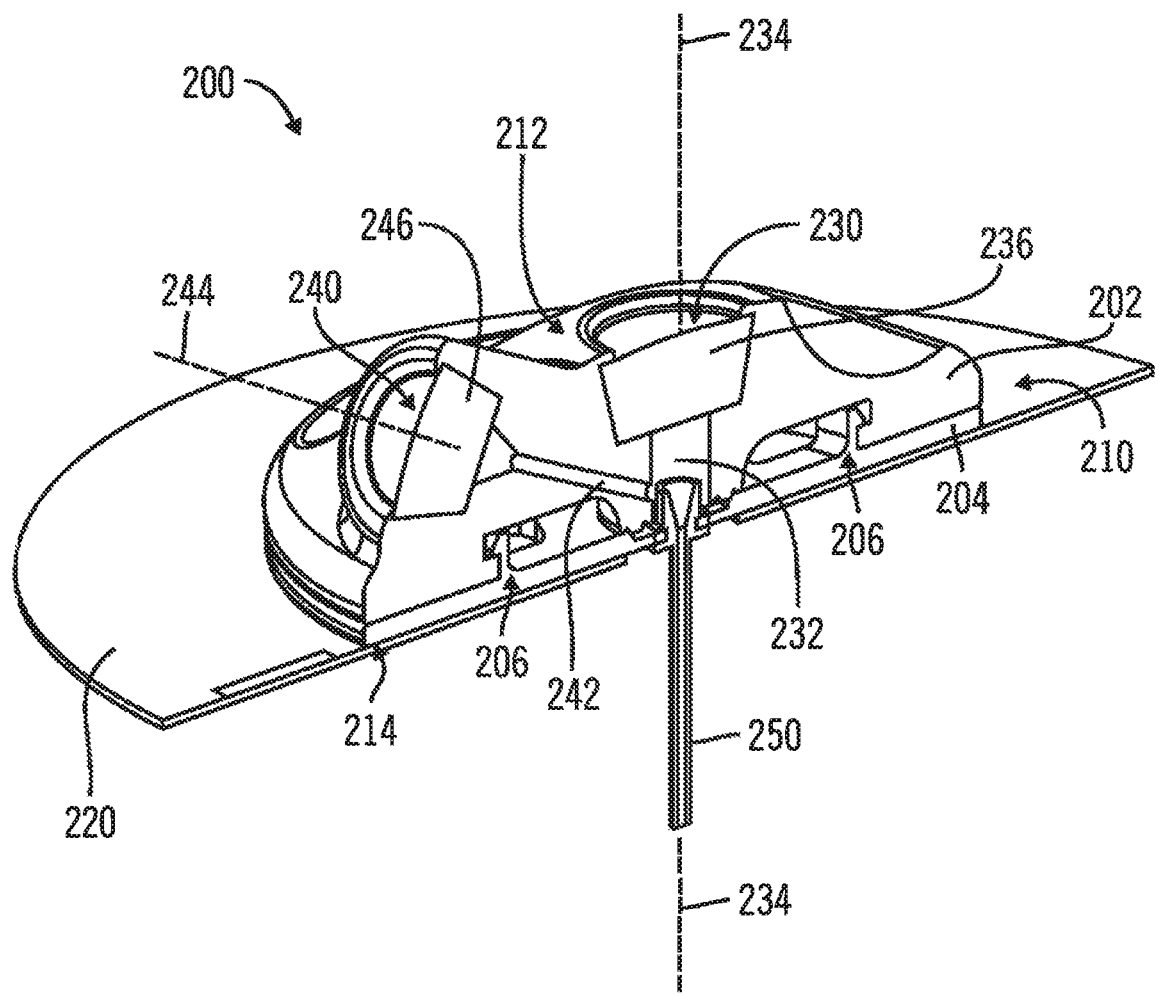
FIG. 6 is a section perspective view of one embodiment of an injection device made in accordance with the invention.

FIG. 6 is a section perspective view of one embodiment of an injection device made in accordance with the invention. In this embodiment, an upper body portion is rotatable about the introducer axis independent of a lower body portion, so that the injection axis can be positioned at a desired rotary angle regardless of the initial placement of the patch on the patient. This allows the patient to select a rotary position for the injection port that is convenient for injection of the therapeutic agent.

The body of the injection device can have a first body portion including the port face and a second body portion including the patient face, the first body portion and the second body portion being rotatably connected with a flange, the first body portion and the second body portion being independently rotatable about the introducer axis.

The body 210 of the injection device 200 includes an upper body portion 202 and a lower body portion 204. The upper body portion 202 and lower body portion 204 are rotatably connected with a flange 206 so that the upper body portion 202 and the lower body portion 204 can rotate independently about the introducer axis 234 defined by the delivery tube 250 along the introducer channel 232. The upper body portion 202 has a port face 212 and the lower body portion 204 has a patient face 214. A patch 220 is attached to the patient face 214 and is operable to adhesively attach the injection device 100 to a patient (not shown).

The delivery tube 250 for subcutaneous delivery of a therapeutic agent projects from and is generally perpendicular to the patient face 214. The delivery tube 250 is operably connected to the introducer port 230, the delivery tube 250 being in fluid communication with the injection port 240. The introducer port 230 includes an introducer channel 232, with an introducer septum 236 disposed in the introducer channel 232. The injection port 240 includes an injection channel 242 defining an injection axis 244 with an injection septum 246 disposed in the injection channel 242.

The injection axis 244 is non-collinear with the introducer axis 234. In this embodiment, the injection axis 244 is at an angle to and intersects with the introducer axis 234. In one example, the delivery tube 250 is a flexible cannula and a needle hub assembly can be used to place the delivery tube 250 subcutaneously in the patient. In another example, the delivery tube 250 is a rigid needle and the delivery tube 250 can be placed subcutaneously in the patient with or without a needle hub assembly.

In operation, the patch 220 is attached to the patient and the delivery tube 250 inserted in the patient for subcutaneous delivery of a therapeutic agent. The injection port 240 in the upper body portion 202 can be rotated about the introducer axis 234 even though the lower body portion 204 is at a fixed position on the patient since the lower body portion 204 is attached to the patient by the patch 220.

FIGS. 7-11, in which like elements share like reference numbers, are various views of one embodiment of an injection device made in accordance with the invention. The injection device includes an introducer port along an introducer axis and an injection port along an injection axis, with the injection axis being non-collinear with the introducer axis. In this embodiment, the injection axis is parallel to and does not intersect with the introducer axis.

The injection device for delivering a therapeutic agent to a patient can include a body, the body having a patient face and a port face opposite the patient face, the port face having an introducer port including an introducer channel and an injection port including an injection channel, the introducer channel being in fluid communication with the injection channel through a cross channel, the injection channel defining an injection axis; a delivery tube for subcutaneous delivery of the therapeutic agent to the patient, the delivery tube projecting from and being generally perpendicular to the patient face, the delivery tube defining an introducer axis and being in fluid communication with the injection port; and a patch, the patch being attached to the patient face and being operable to adhesively attach to the patient; wherein the injection axis is parallel to the introducer axis.

In some embodiments, the parallel injection axis and introducer axis allows the injection device to function as both an injection device and sensor support. In such embodiments to prevent the sensor from obtaining spurious readings caused by introduction of the therapeutic fluid the introducer channel and injection port would not be in fluid communication. In such embodiments either the introducer channel or the injection port could be adapted to support the insertion and continuous wearing of a sensor. In some embodiments the sensor could be worn for two days before needing to be replaced. In other embodiments the sensor could be worn for up to 14 days before needing to be replaced. Additionally, in some embodiments the sensor would measures glucose values in subcutaneous tissue and associated electronics are able to determine a corresponding blood glucose value.

Figure 7:
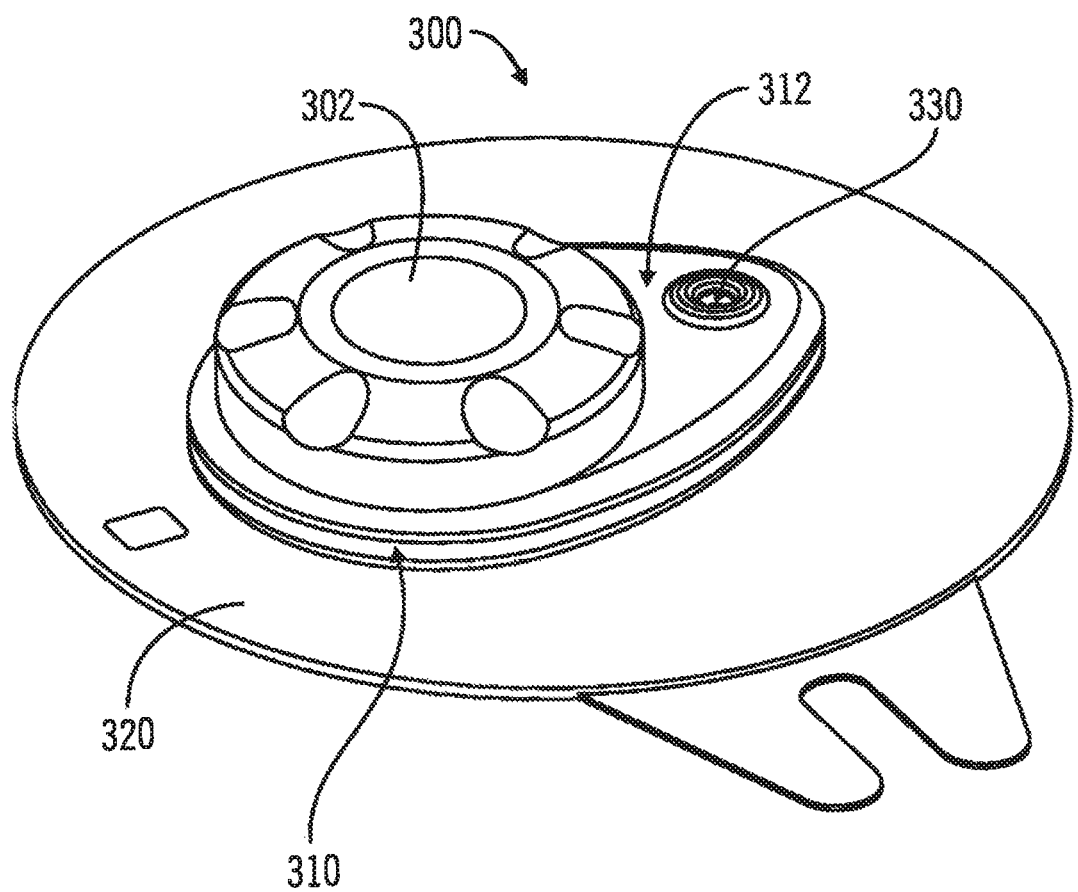
FIGS. 7-8 are perspective views, respectively, of one embodiment of an injection device made in accordance with the invention.

FIG. 7 is a perspective view of the injection device 300 including a body 310 and a patch 320 attached to the body 310. The patch 320 is operable to adhesively attach the injection device 300 to a patient (not shown). The body 310 has a port face 312, with an introducer port 330 on the port face 312. The introducer port 330 is used to place a delivery tube subcutaneously in the patient. In this example, an optional injection cap 302 secured to the body 310 to protect an injection port, which is used by the patient to inject a therapeutic agent.

Figure 8:
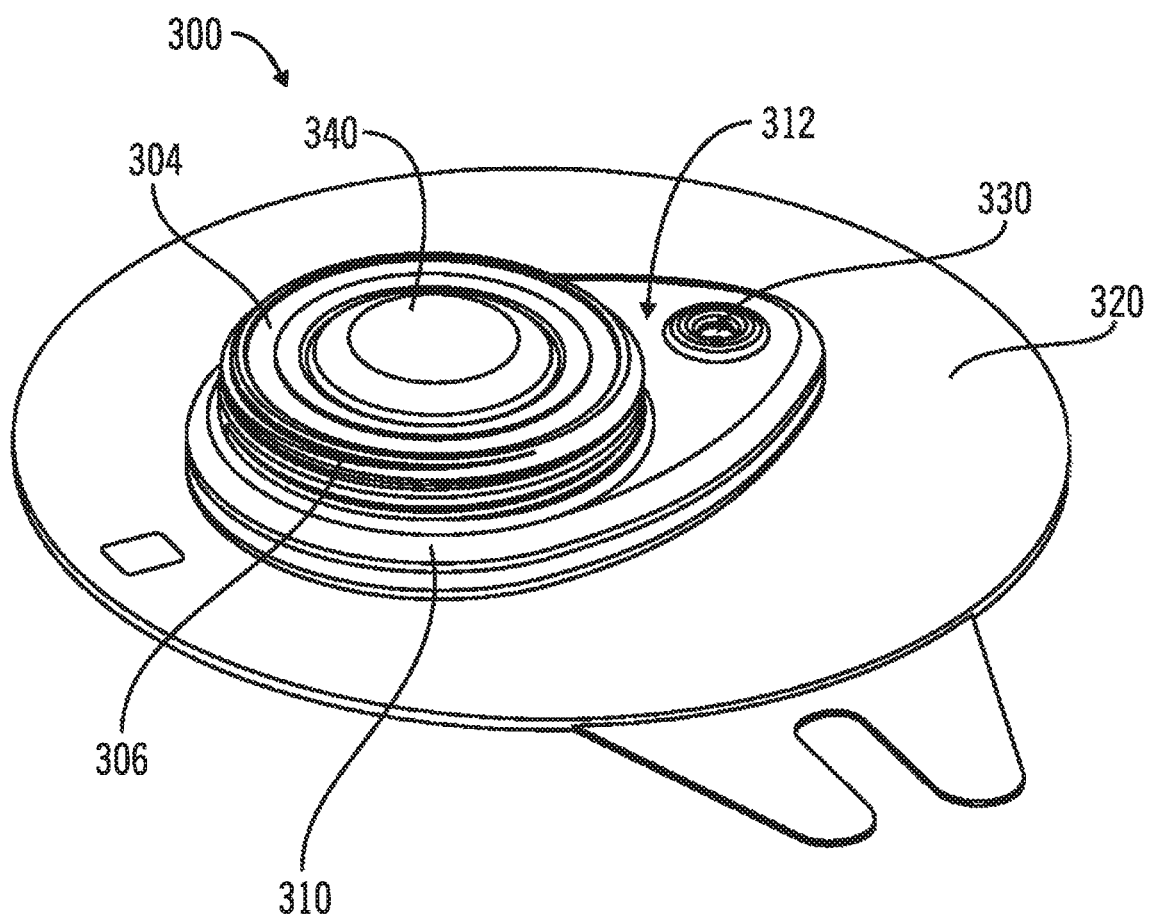

FIG. 8 is a perspective view of the injection device 300 with the optional injection cap removed to expose the injection port 340. In this example, the body 312 includes threads 306 to secure the optional injection cap to the body and an optional O-ring 304 to seal the area around the injection port 340 when the optional injection cap is secured to the body.

Figure 9A:
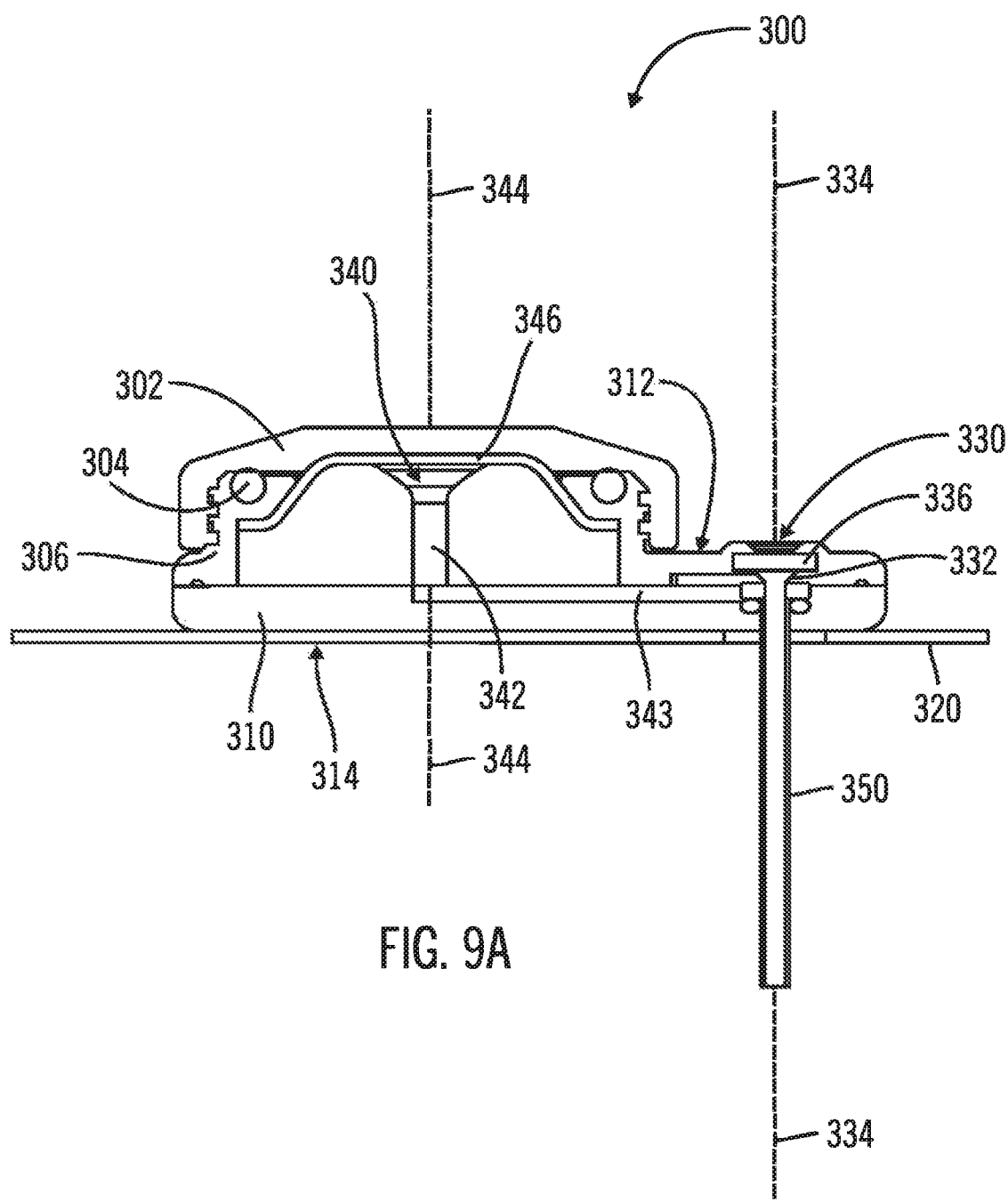
FIGS. 9A-9B are section views of one embodiment of an injection device made in accordance with the invention.

FIG. 9A is a section view of the injection device 300, the section bisecting the introducer port 330 and the injection port 340 and including the introducer axis 334 and injection axis 344. The body 310 has a port face 312 and a patient face 314. A delivery tube 350 for subcutaneous delivery of the therapeutic agent projects from and is generally perpendicular to the patient face 314. The delivery tube 350 is operably connected to the introducer port 330 and defines an introducer axis 334 along the introducer channel 332, the delivery tube 350 being in fluid communication with the injection port 340. The introducer port 330 includes an introducer channel 332, with an introducer septum 336 disposed in the introducer channel 332. The injection port 340 includes an injection channel 342 defining an injection axis 344 with an injection septum 346 disposed over the injection channel 342. In this embodiment, the injection axis 344 is parallel to and does not intersect with the introducer axis 334. A cross channel 343 connects the injection channel 342 to the introducer channel 332. In one example, the delivery tube 350 is a flexible cannula and a needle hub assembly can be used to place the delivery tube 350 subcutaneously in the patient. In another example, the delivery tube 350 is a rigid needle and the delivery tube 350 can be placed subcutaneously in the patient with or without a needle hub assembly.

Figure 9B:
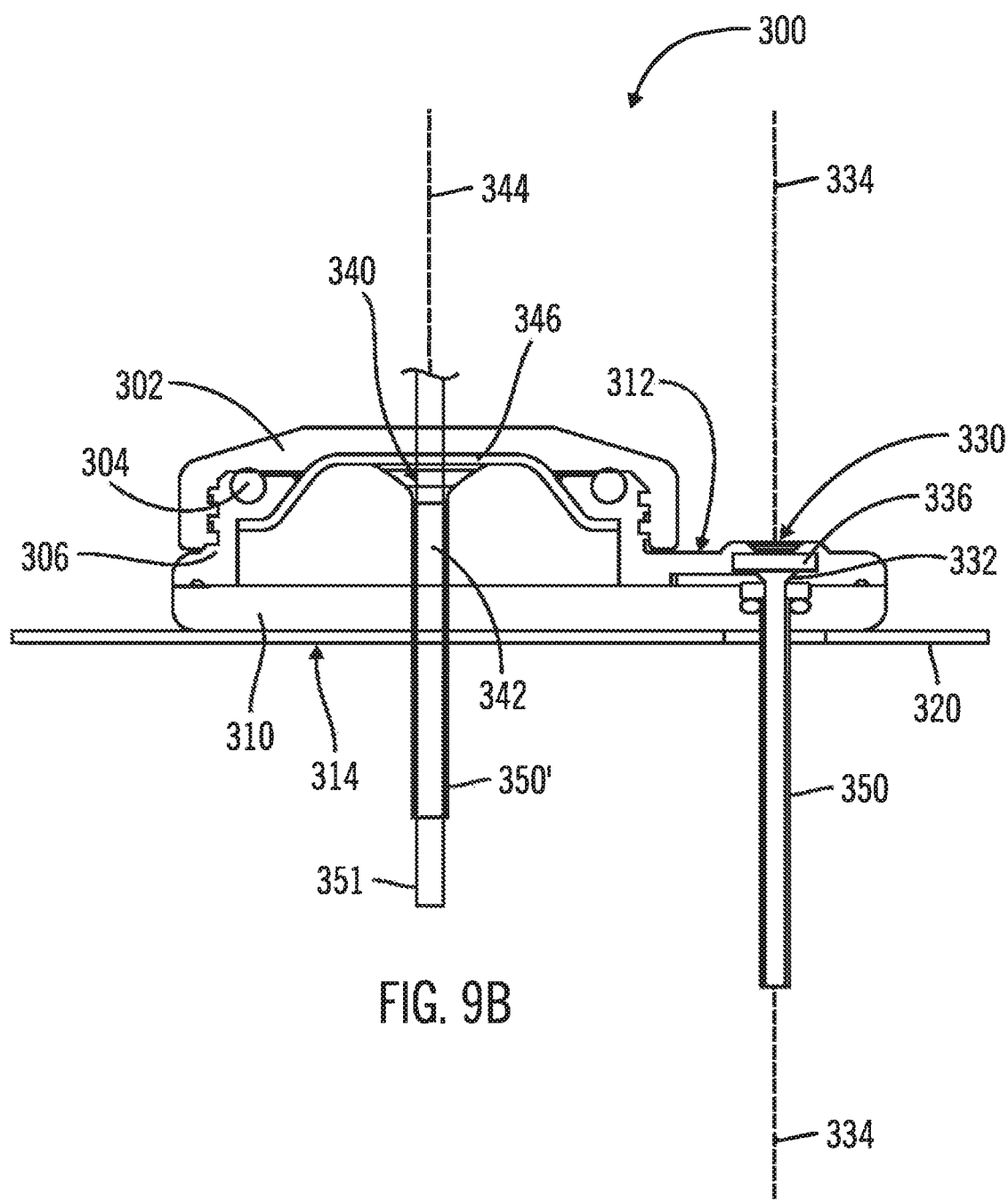

FIG. 9B is a section view of a different embodiment of injection device 300, the section bisecting the introduced port 330 and the injection port 340 and including the introducer axis 334 and injection axis 344. The body 310 includes a port face 312 and a patient face 314. A delivery tube 350 for subcutaneous delivery of the therapeutic agent projects from and is generally perpendicular to the patient face 314. The delivery tube 350 is operably connected to the introducer port 330 and defines an introducer axis 334 along the introducer channel 332. The introducer port 330 includes an introducer channel 332, with an introducer septum 336 disposed in the introducer channel 332. The injection port 340 includes an injection channel 342 defining an injection axis 344 with an injection septum 346 disposed over the injection channel 342. In this embodiment, the injection axis 344 is parallel and does not intersect with the introducer axis 334. In this embodiment a delivery tube 350' is also found operably connected to the injection port 340. The cross channel 343 found in FIG. 9A is not found in this embodiment enabling a sensor 351 to be placed into the delivery tube 350' via injection port 340 while therapeutic agents can still be delivered via delivery tube 350 and introducer port 330. In other embodiments the sensor 351 is placed through delivery tube 350 and introducer port 330 while therapeutic agents are administered via delivery tube 350' and injection port 340.

In some embodiments the sensor 351 is a glucose sensor similar to, but not limited to the Enlite Sensor made by Medtronic. In these embodiments the sensor is inserted into the subcutaneous tissue and then connected to sensor electronics. In some embodiments the sensor electronics are contained within a sealed housing that includes an opening to receive sensor contacts disposed on an end that remains outside the injection device. Physical contact is made between the sensor electronics and the sensor contacts to provide power from the sensor electronics that initiates chemical reactions between the sensor and fluid within the subcutaneous tissue. The sensor electronics housing includes coupling features to removably couple the sensor electronics to the port face 312. In some embodiments the coupling features are compatible screw threads, while in other embodiments the coupling features are quarter turn features or quick release snap type features. The types of coupling features described above are intended to be exemplary and should not be construed as limiting. Additional coupling features can be used that enable quick and secure coupling between the sensor electronics housing and the port face 312.

Figure 10:
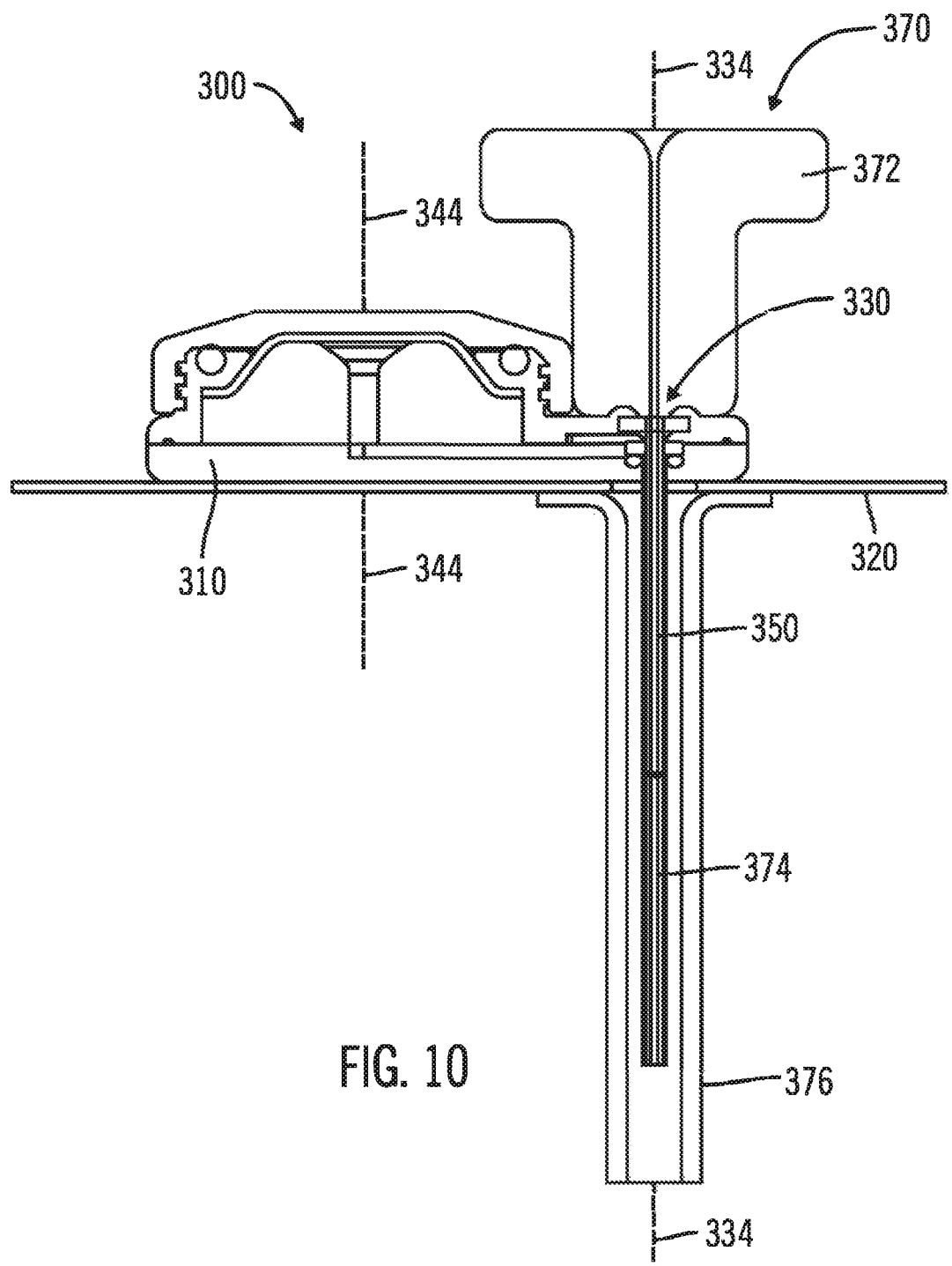
FIGS. 10-11 are section and perspective section views, respectively, of one embodiment of an injection device made in accordance with the invention.

FIG. 10 is a section view of the injection device 300 with a needle hub assembly 370 and a needle guard 376. The needle hub assembly 370 includes a needle hub 372 and a needle 374 attached to the needle hub 372. The needle 374 of the needle hub assembly 370 is inserted through the introducer port 330 and through the delivery tube 350 along the introducer axis 334. The needle hub assembly 370 can be used to add rigidity to the delivery tube 350 when the delivery tube 350 is a flexible cannula. The needle hub assembly 370 can optionally be used when the delivery tube 350 is a rigid needle. A needle guard 376 disposed around the needle 374 can be used to protect the needle 374 and the delivery tube 350 when the injection device and needle hub assembly are assembled for shipping.

Figure 11:
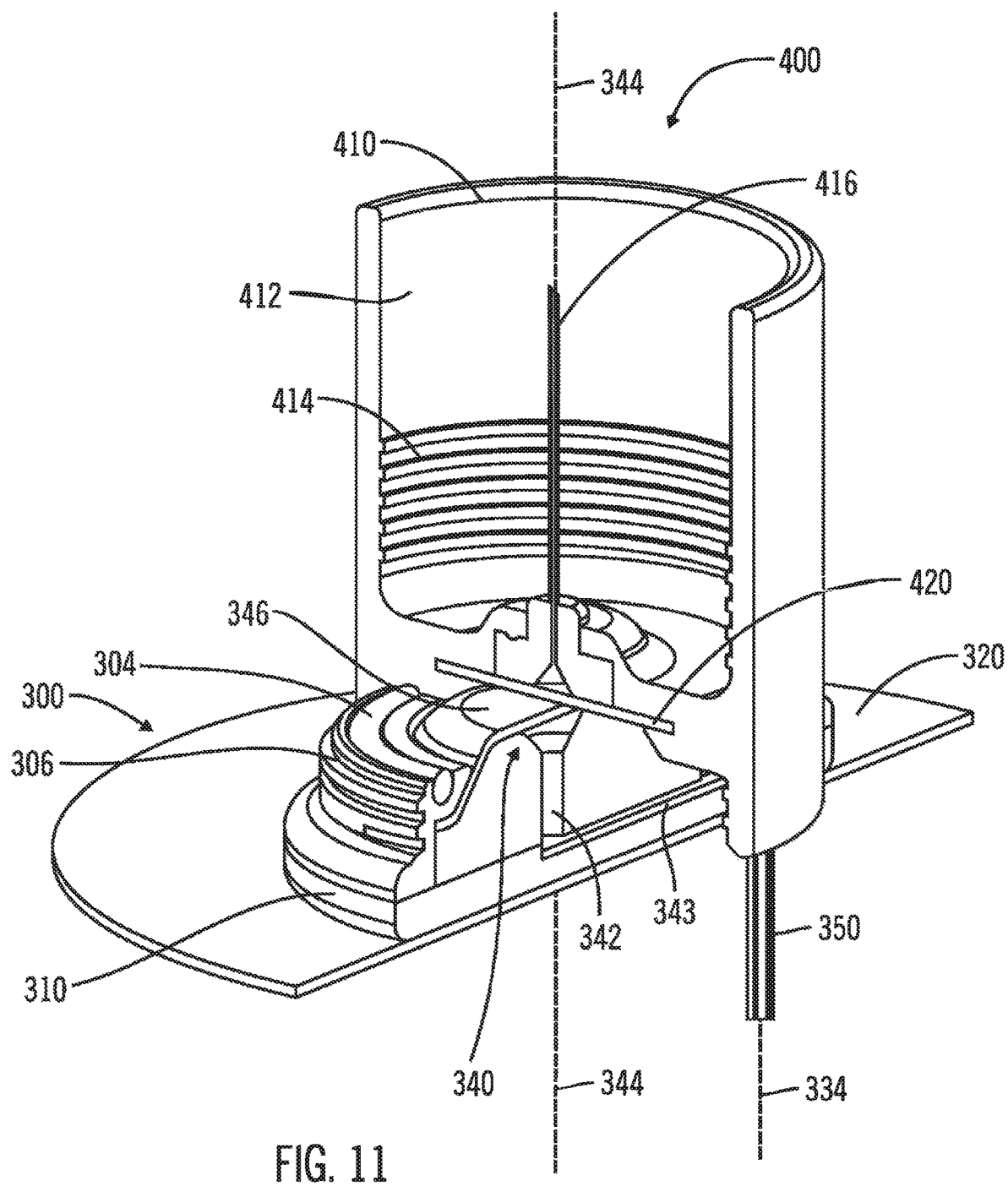

FIG. 11 is a perspective section view of the injection device with an injection adapter assembly. For clarity of illustration, the cross section cut of the injection device 300 in the illustration bisects the introducer port 330 and the injection port 340, and includes the introducer axis 334 and injection axis 344. The cross section cut of the injection adapter assembly 400 in the illustration includes the injection axis 344 and is perpendicular to the section of the injection device 300. The injection adapter assembly 400 screws onto the injection device 300 using the threads 306 on the body 310 to secure the needleless pen injector to the body 310, with the O-ring 304 sealing around the interface between the adapter septum 420 and the injector septum 346. Those skilled in the art will appreciate that the mateable connection securing the needleless pen injector to the body is not limited to threads and can be any mateable connection desired for a particular application.

In this embodiment, the injection adapter assembly 400 is adapted to receive a needleless pen injector (not shown). The adapter body 410 defines a recess 412 adapted to receive a tip of the needleless pen injector. In this example, the needleless pen injector includes threads on its outer diameter complementary to the adapter threads 414 on the inner diameter of the adapter body 410. The tip of the needleless pen injector is screwed into the recess 412 so that the adapter needle 416 is received in the needleless pen injector, accessing the therapeutic agent contained within the needleless pen injector by piercing a foil on the tip of the needleless pen injector or accessing a pen injector port adapted to receive the adapter needle 416. With the needleless pen injector secured in the injection adapter assembly 400, pressure applied to the therapeutic agent enclosed in the needleless pen injector forces the therapeutic agent through the adapter needle 416 and the adapter septum 420 into the injection device 300, where the therapeutic agent passes through the injector septum 346 into the injection port 340, through the injection channel 342, the cross channel 343, and the delivery tube 350, and into the patient.

Those skilled in the art will appreciate that a variety of interfaces can be used between the needleless pen injector, the injection adapter assembly 400, and the injection device 300. In the embodiment of FIG. 11, the adapter septum 420 and the injector septum 346 are permeable so that the therapeutic agent passes through the adapter septum 420 and the injector septum 346. The septums can be hydrophilic when used with the needleless pen injector to allow the therapeutic agent to pass through. In another embodiment, the injector septum can include a slit valve operable to open on receiving a stub tube at the tip of the needleless pen injector. In yet another embodiment, the injector septum can include a slit valve which is open by a mechanical lever that pushes open and spread the slit valve when the needleless pen injector is received in the injection adapter assembly. In yet another embodiment, the needleless pen injector is interlocked with the injection adapter assembly so that no therapeutic agent can be dispensed from the needleless pen injector until the needleless pen injector is fully engaged with the injection adapter assembly.

FIGS. 12A-12D are various views of needleless pen injectors for use with an injection device made in accordance with the invention. Each of the needleless pen injectors is provided with a manual or automatic pressurization to force the therapeutic agent held within the needleless pen injector into the injection device and patient, once the needleless pen injector has been fully engaged with an injection adapter assembly.

Figure 12A:
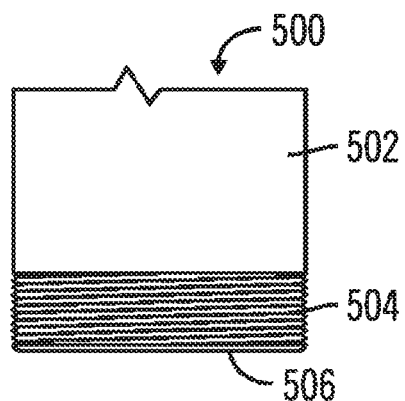
FIGS. 12A-12D are side and section views of needleless pen injectors for use with an injection device made in accordance with the invention.
Figure 12B:
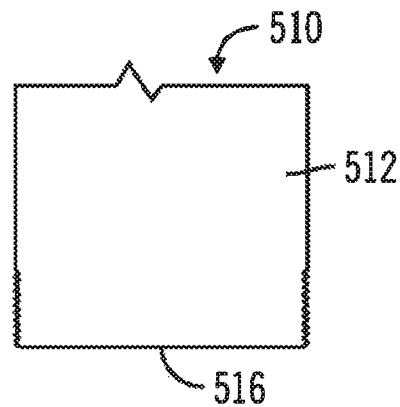
Figure 12C:
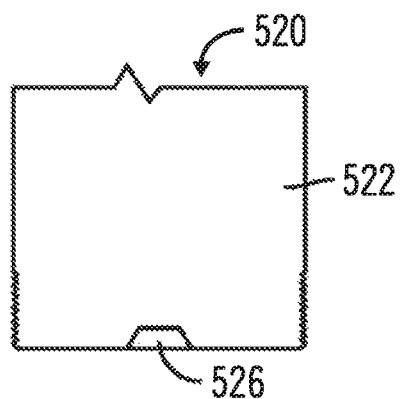
Figure 12D:
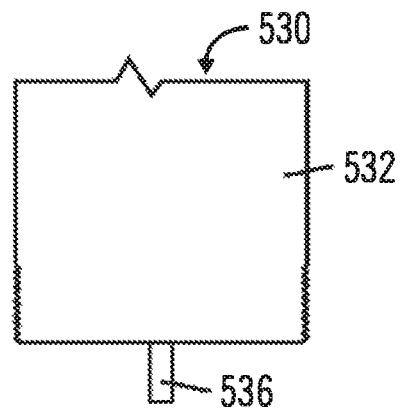

FIG. 12A is a side view of the tip of a needleless pen injector 500 having a barrel 502 to contain a therapeutic agent and optional threads 504 for use with an adapter body having threads on the inner diameter. The end 506 of the needleless pen injector 500 can be adapted to accommodate the particular design of an injection adapter assembly for a particular application. FIG. 12B is a section view of the tip of a needleless pen injector 510 having a barrel 512 to contain a therapeutic agent and a foil 516 across the end of the needleless pen injector 510. The foil 516 can be pierced by an adapter needle in the injection adapter assembly (shown in FIG. 11) to provide fluid communication between the needleless pen injector 510 and the injection device through the injection adapter assembly. FIG. 12C is a section view of the tip of a needleless pen injector 520 having a barrel 522 to contain a therapeutic agent and a pen port 526 at the end of the needleless pen injector 520. The pen port 526 can receive an adapter needle in the injection adapter assembly (shown in FIG. 11) to open the pen port 526 and provide fluid communication between the needleless pen injector 520 and the injection device through the injection adapter assembly. FIG. 12D is a section view of the tip of a needleless pen injector 530 having a barrel 532 to contain a therapeutic agent and a stub tube 536 at the end of the needleless pen injector 530. The stub tube 536 is operable to open a slit valve on the injector septum of the injection device.

FIGS. 13A-13F, in which like elements share like reference numbers, are section views of pop-up indicator ports for use with an injection device made in accordance with the invention. Because the introducer port and the injection port of the injection device are both in fluid communication with the delivery tube, flow blockage in the delivery tube can cause an increase in pressure at both ports when the patient attempts to inject a therapeutic agent. The flow blockage/pressure increase can be detected by the patient, indicating that the therapeutic agent is not being delivered, with a pop-up indicator port in the port not being used for injection. During injection, the membrane of the pop-up indicator port is close to the body of the injection device under normal conditions, and extends from the body of the injection device when the delivery tube is blocked and the pressure increases above a predetermined pressure.

The pop-up indicator can be disposed in the introducer channel, the pop-up indicator having a normal state when pressure in the introducer channel is normal and an alarm state when pressure in the introducer channel exceeds a predetermined value.

Figure 13A:
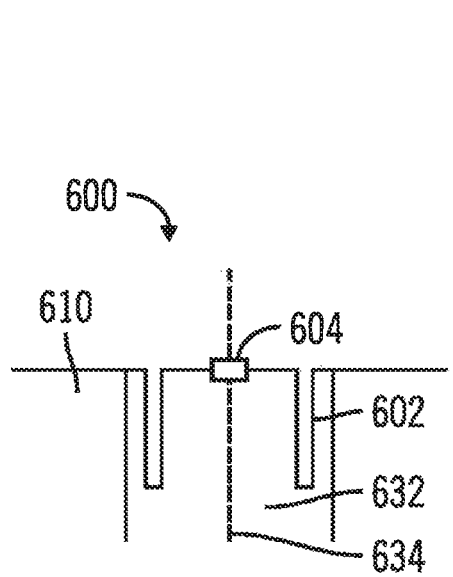
FIGS. 13A-13F are section views of pop-up indicator ports for use with an injection device made in accordance with the invention.
Figure 13B:
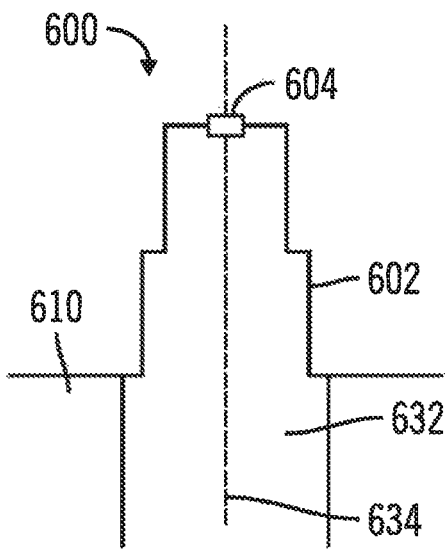

FIGS. 13A & 13B are section views of a pop-up indicator port 600 with a folded membrane 602 installed as the introducer port. The pop-up indicator port 600 is installed in the introducer channel 632 of the body 610 along the introducer axis 634, and is in fluid communication with the injection channel. A self-closing port 604 in the membrane 602 allows a needle of a needle hub assembly to pass through the membrane 602 when a needle hub assembly is used to implant the injection device. No self-closing port is required if a needle hub assembly is not used to implant the injection device. Referring to FIG. 13A, the pop-up indicator port 600 is in the normal state with normal pressure in the introducer channel 632, with the membrane 602 folded on itself. Referring to FIG. 13B, the pop-up indicator port 600 is in the alarm state due to pressure in the introducer channel 632 exceeding a predetermined value. The pressure occurs when a therapeutic agent is being injected into the injection port, which is in fluid communication with the introducer channel 632, while the delivery tube is blocked. In the alarm state, the membrane 602 unfolds to extend from the body 610.

Figure 13C:
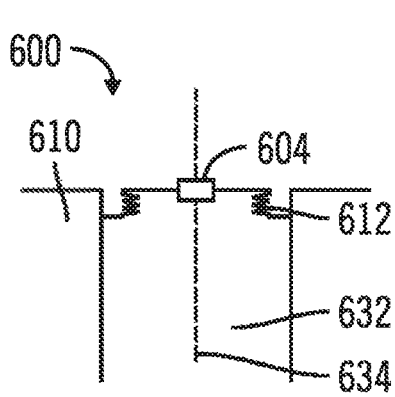
Figure 13D:
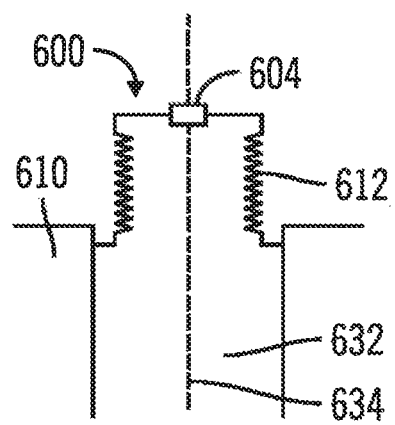

FIGS. 13C & 13D are section views of a pop-up indicator port 600 with an accordion membrane 612 installed as the introducer port. Referring to FIG. 13C, the pop-up indicator port 600 is in the normal state with normal pressure in the introducer channel 632, with the membrane 612 pleated like an accordion. Referring to FIG. 13D, the pop-up indicator port 600 is in the alarm state due to pressure in the introducer channel 632 exceeding a predetermined value. The pressure occurs when a therapeutic agent is being injected into the injection port, which is in fluid communication with the introducer channel 632, while the delivery tube is blocked. In the alarm state, the membrane 612 uncompresses the pleats to extend from the body 610.

Figure 13E:
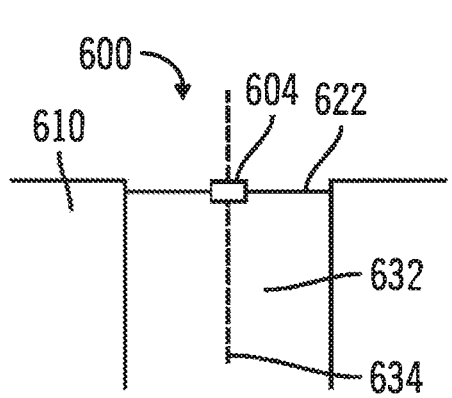
Figure 13F:
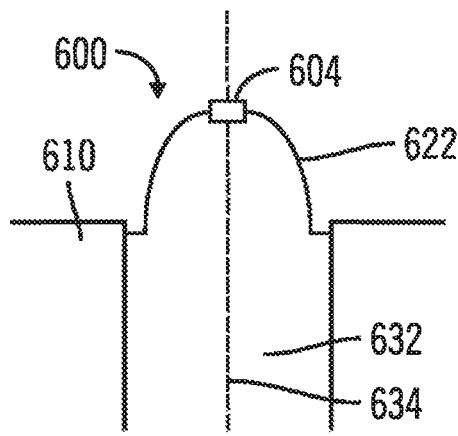

FIGS. 13E & 13F are section views of a pop-up indicator port 600 with a deformable membrane 622 installed as the introducer port. Referring to FIG. 13E, the pop-up indicator port 600 is in the normal state with normal pressure in the introducer channel 632, with the membrane 622 extending across the introducer channel 632. Referring to FIG. 13F, the pop-up indicator port 600 is in the alarm state due to pressure in the introducer channel 632 exceeding a predetermined value. The pressure occurs when a therapeutic agent is being injected into the injection port, which is in fluid communication with the introducer channel 632, while the delivery tube is blocked. In the alarm state, the material of the membrane 622 deforms under pressure to extend from the body 610. In another embodiment, the material of the membrane 622 can deforms sufficiently to allow the therapeutic agent to leak through the membrane 622, providing additional indication of the high pressure and delivery tube blockage.

Those skilled in the art will appreciate that the material and dimensions of the parts of the membrane (folds and/or pleats) can be selected as desired for a particular application. In one embodiment, the material is resilient, so that the membrane returns to the normal state after being in the alarm state. In another embodiment, the material is deformable so that the membrane remains extending from the body after the pressure is relieved and the alarm state clears. The extended membrane reminds the patient of the delivery tube blockage and the need to replace the injection device. Exemplary materials for the membrane include silicone rubber or the like.

Figure 14A:
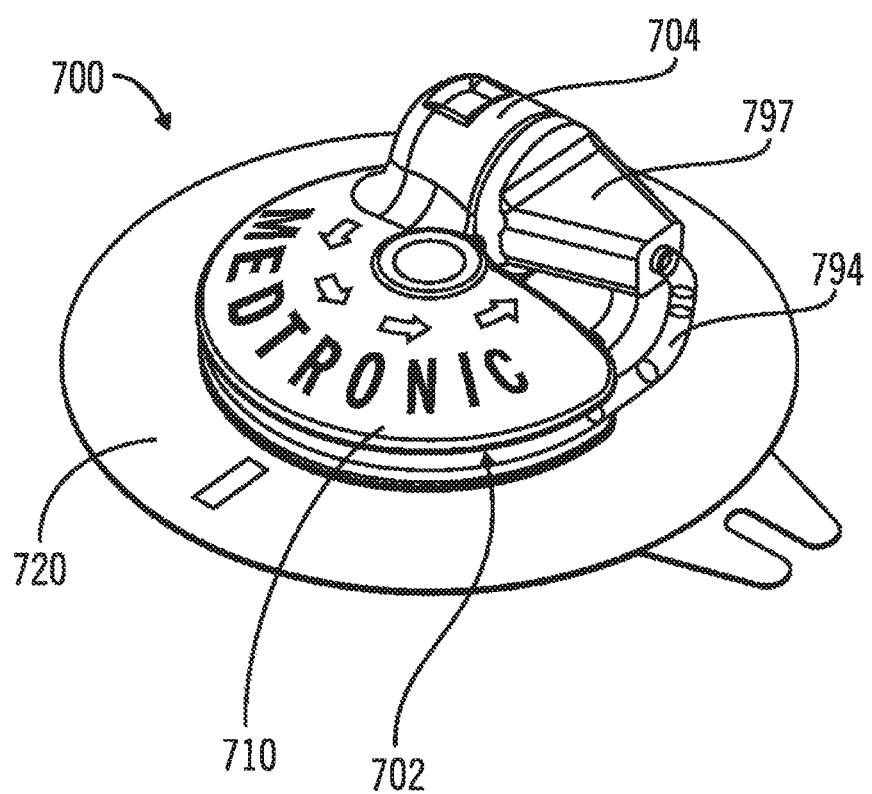
FIGS. 14A & 14B are perspective views of one embodiment of an injection device made in accordance with the invention.
Figure 14B:
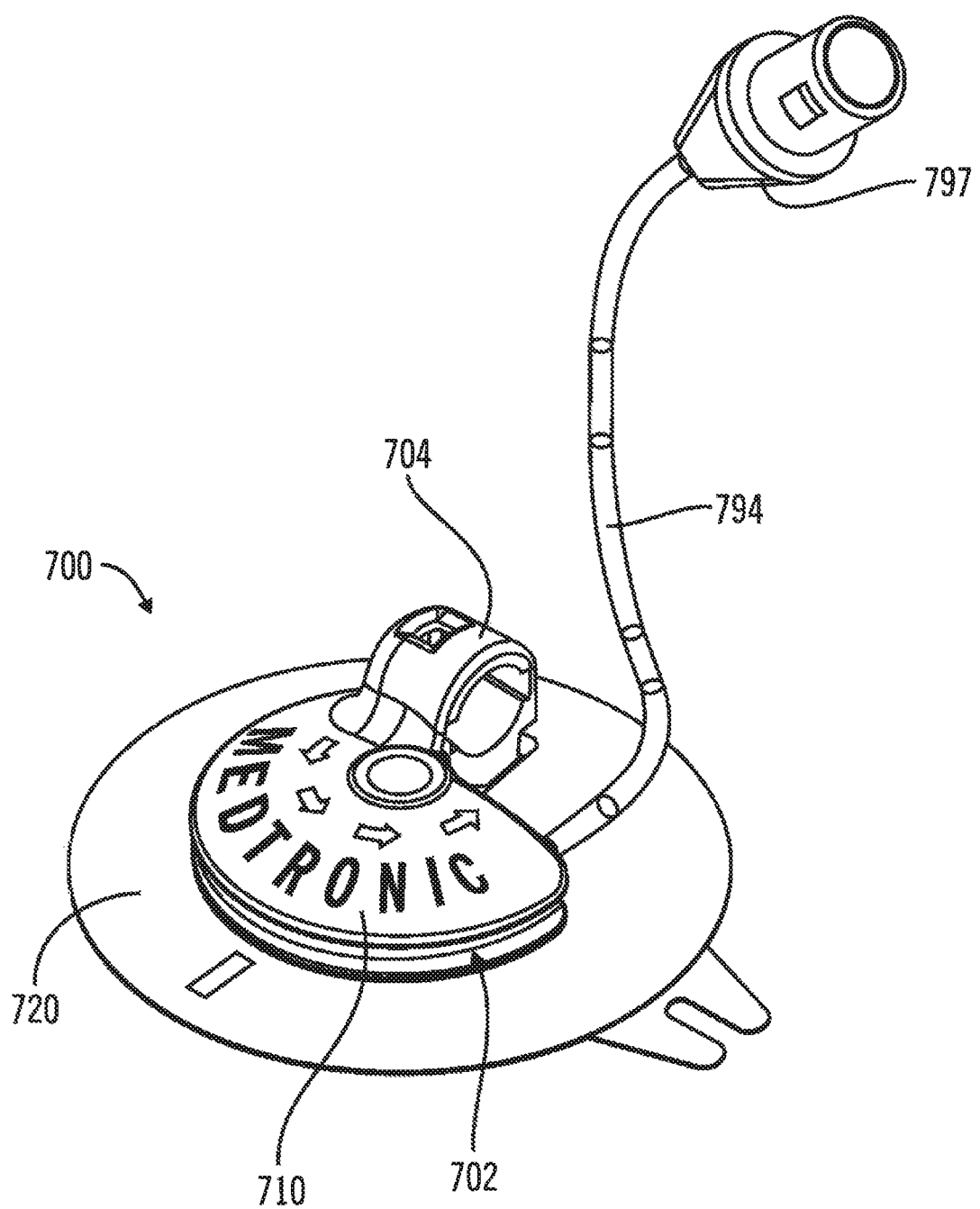

FIGS. 14A & 14B, in which like elements share like reference numbers, are perspective views of one embodiment of an injection device made in accordance with the invention. In this embodiment, the injection device includes a tube with an external device fitting, so that the injection device can be placed in a remote location and attached to an injection pump.

FIG. 14A is a perspective view of the injection device 700 in a stored configuration, the injection device 700 including a body 710 and a patch 720 attached to the body 710. The patch 720 is operable to adhesively attach the injection device 700 to a patient (not shown). The body 710 has a groove 702 around its outer circumference operable to receive tube 794 in the stored configuration. One end of the tube 794 is in fluid communication with an injection port (not shown) of the injection device 700 to deliver a therapeutic agent into the body of a patient. The other end of the tube 794 is in fluid communication with the external device fitting 797, which can be extended to a convenient location when the injection device 700 is in a difficult to access location or which can be connected to an injection pump (not shown). In this example, the body 710 includes a fitting receiver 704 operable to receive and store the external device fitting 797 when the injection device 700 is in the stored configuration with the tube 794 wrapped around the body 710. FIG. 14B is a perspective view of the injection device 700 in a deployed configuration, with the external device fitting 797 uncoupled from the fitting receiver 704 and the tube 794 uncoiled from the groove 702 in the body 710. In operation, the injection device 700 can be placed on a remote location on the body of the patient, such as a remote location not normally accessible for injection by conventional means, and the tube 794 extended to allow convenient connection to an injection pump.

FIGS. 15-20, in which like elements share like reference numbers, are various views of one embodiment of a body for an injection device made in accordance with the invention. The body includes cutouts to provide inspection and ventilation at the attachment point of the injection device to the patient.

The single piece body for an injection device can include a planar deck having a patient face, the planar deck having cutouts around and through the planar deck, the planar deck including a delivery tube port on the patient face; a port segment attached opposite the patient face of the planar deck, the port segment including an introducer port including an introducer channel and an injection port including an injection channel the introducer channel being in fluid communication with the injection channel and the delivery tube port; and attachment projections protruding from the patient face. In one embodiment, the attachment projections are operable for plastic welding.

The single piece body can be used with an injection device for delivering a therapeutic agent to a patient including the single piece body. The injection device further includes a delivery tube for subcutaneous delivery of the therapeutic agent to the patient, the delivery tube projecting from and being generally perpendicular to the patient face, the delivery tube being in fluid communication with the injection port; and a patch, the patch being plastically welded to the attachment projections and being operable to adhesively attach to the patient.

Figure 15:
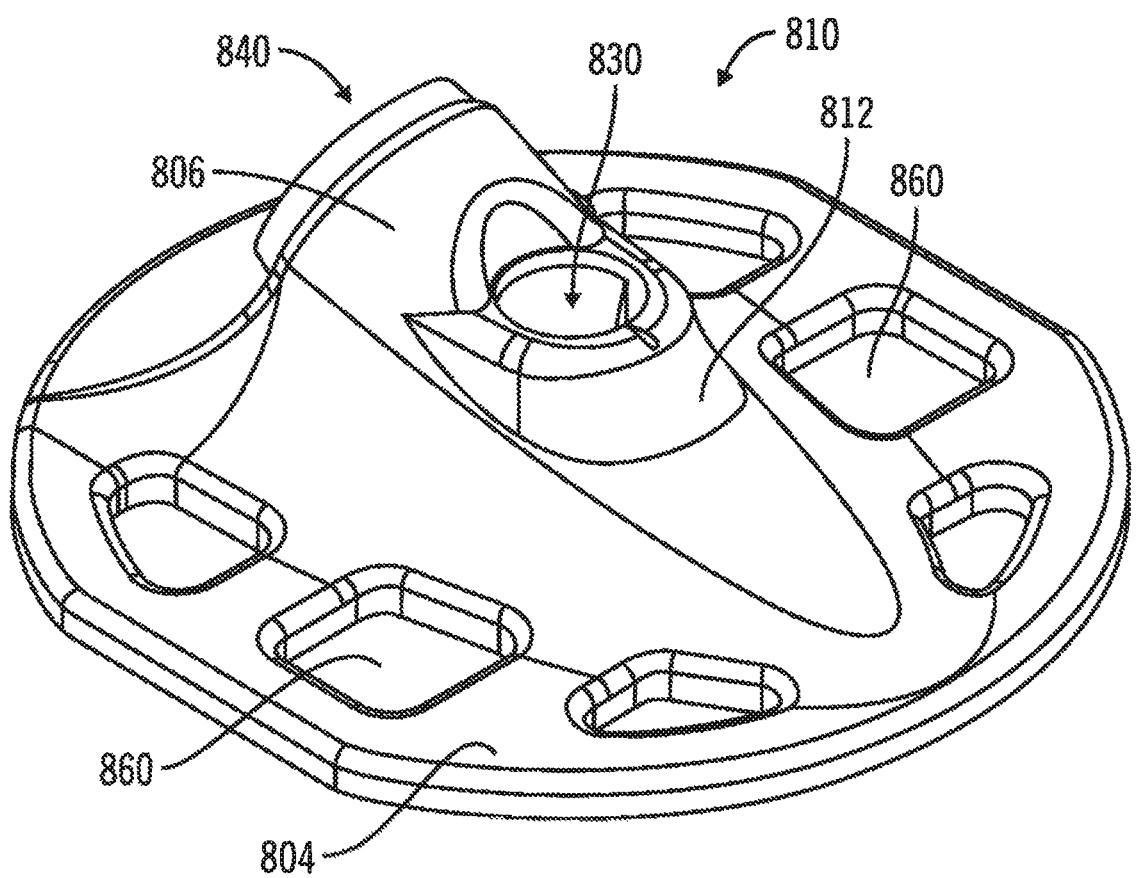
FIGS. 15-20 are front perspective, top side, left side, bottom side, bottom perspective, and detail views, respectively, of one embodiment of a body for an injection device made in accordance with the invention.
Figure 16:
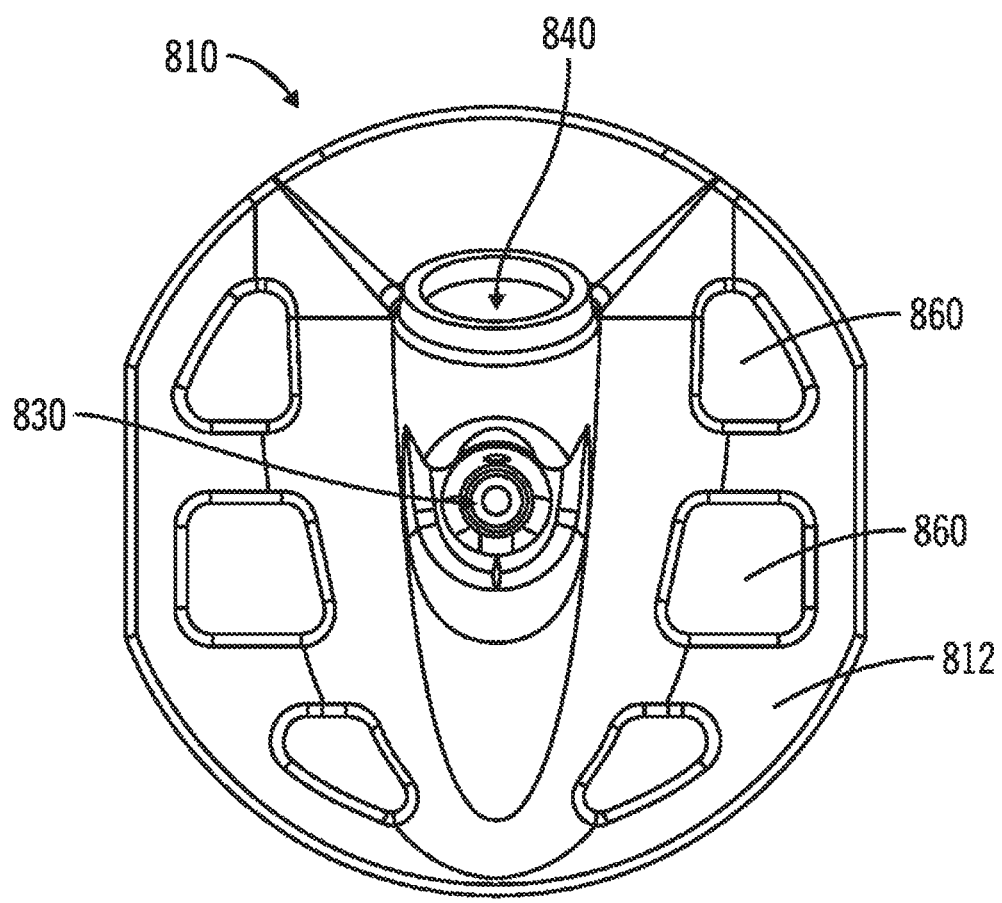

FIGS. 15 & 16 are a front perspective view and a top side view, respectively, of a body 810 including a port face 812. The port face 812 includes an introducer port 830 and an injection port 840. The body 810 has a generally planar deck 804 with cutouts 860 spaced around and passing through the planar deck 804. The body 810 also has a port segment 806 rising above the planar deck 804 and including the introducer port 830 and an injection port 840. The body 810 is a single piece body, which is defined herein as a body formed as a single piece and is not a group of separate pieces assembled to form the body.

Figure 17:
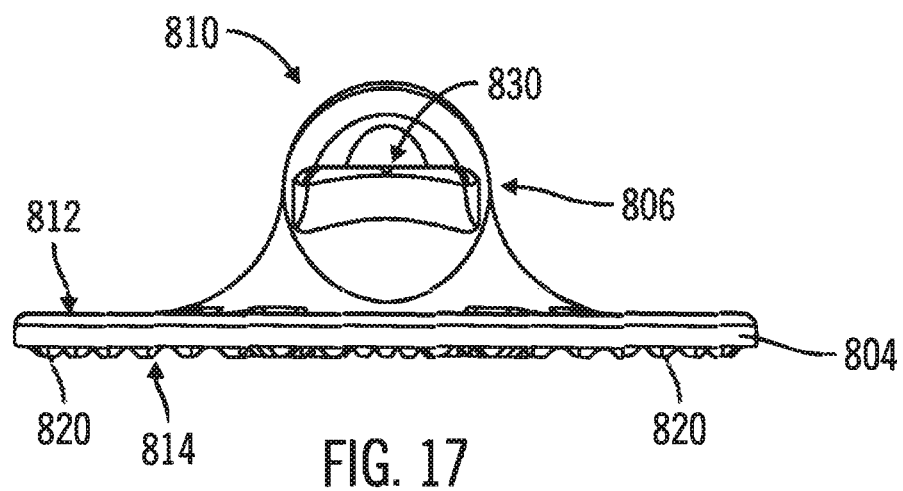

FIG. 17 is a left side view of the body 810. The patient face 814 is opposite the port face 812 on the planar deck 804 and is operable to connect the body 810 to a patch (not shown) to adhesively attach the injection device to a patient. In this embodiment, the patient face 814 of the planar deck 804 includes a number of attachment projections 820 (in this example, the attachment projections 820 being bumps) protruding from the planar deck 804 to allow a patch to be plastically welded to the body 810. Those skilled in the art will appreciate that different attachment projections, such as truncated pyramids, bumps, radial lines, concentric rings, or the like, can be selected as desired for a particular application. In yet another embodiment, the patch can be attached to the body 810 with an adhesive.

Figure 18:
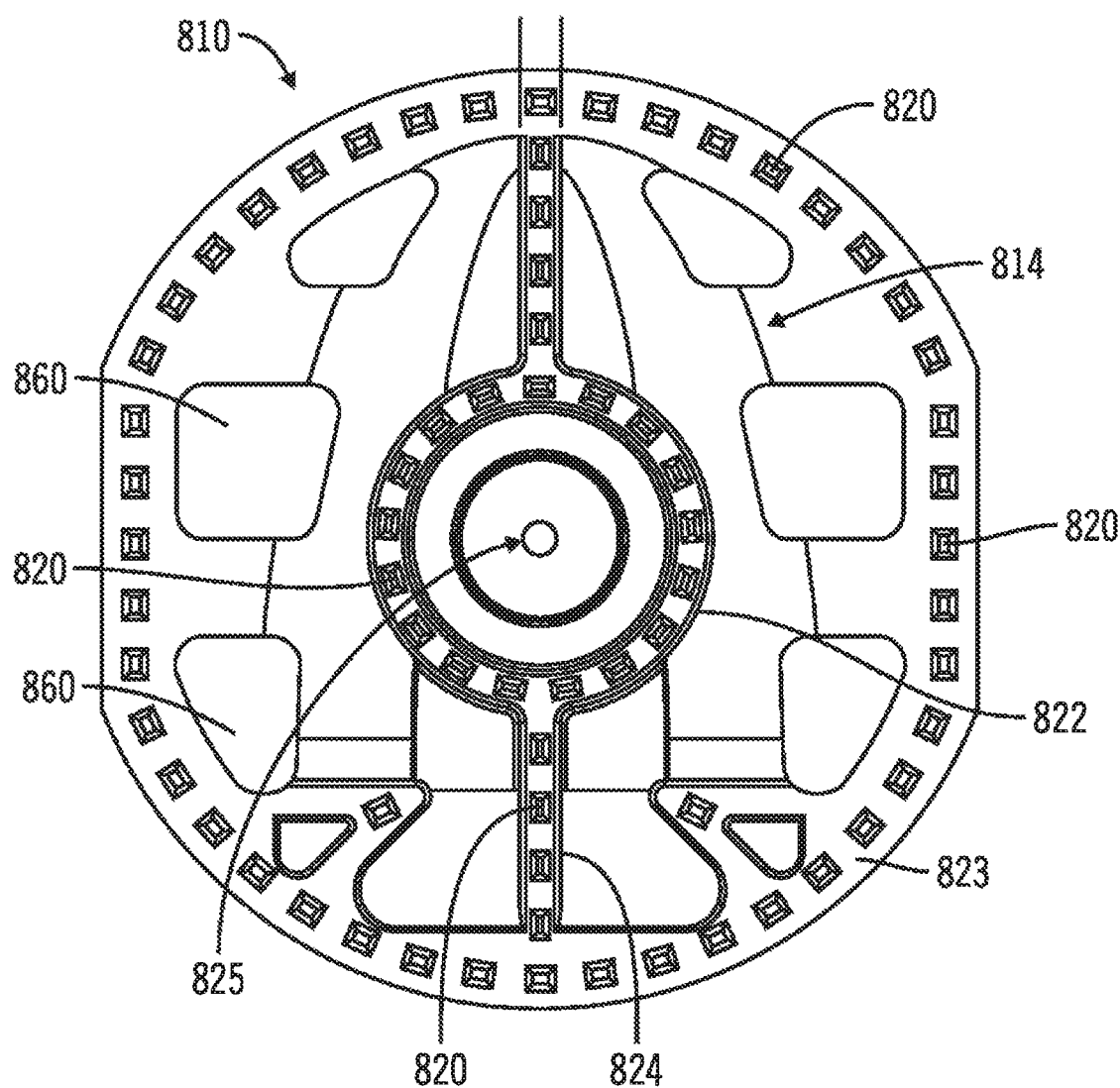
Figure 19:
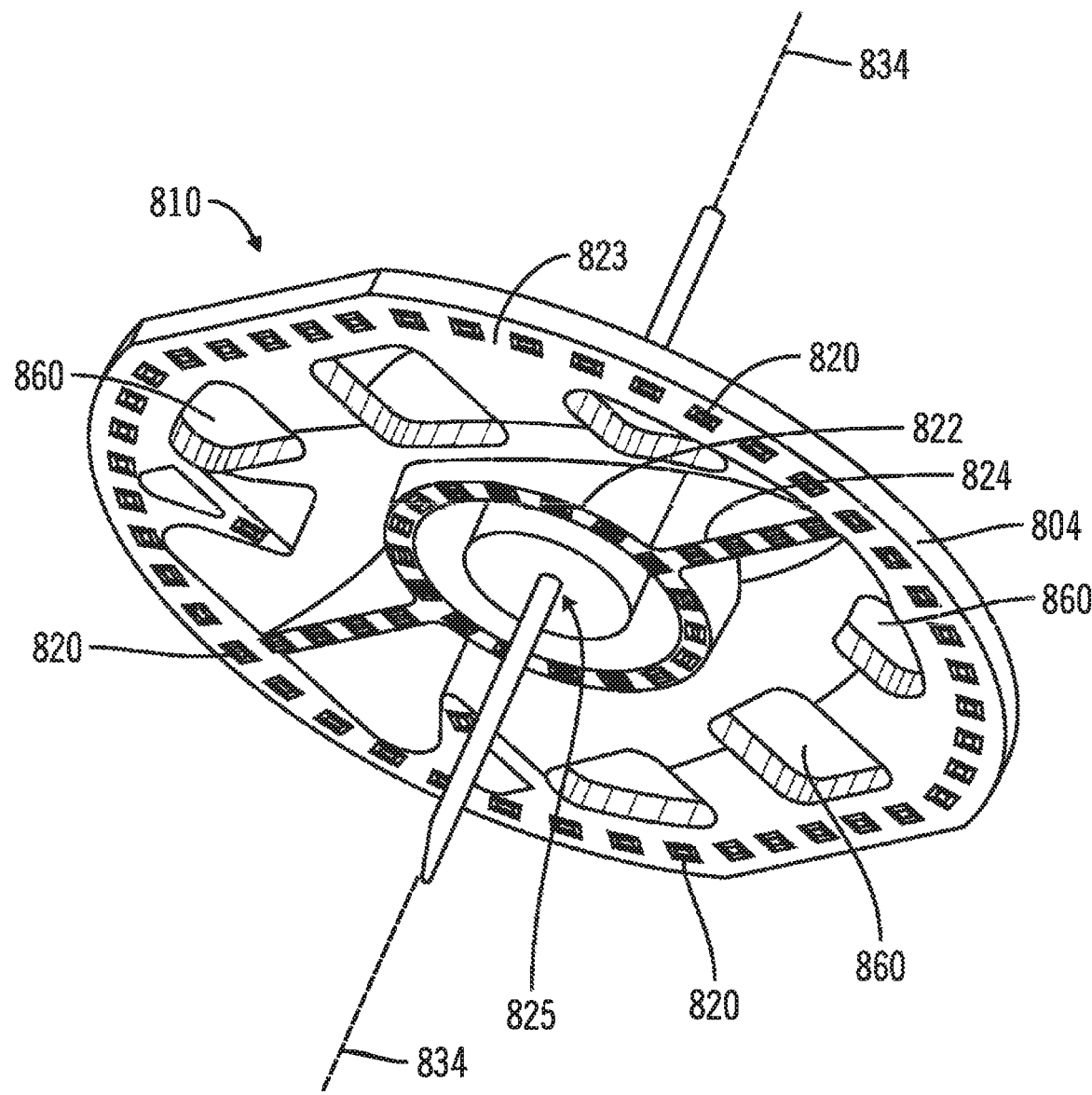

FIGS. 18 & 19 are a bottom side view and a bottom perspective view, respectively, of the body 810. The attachment projections 820 are arranged around the outer circumference 823 of the patient face 814, around an inner circle 822 about a delivery tube port 825 on the introducer axis 834, and along diameter segments 824 between the outer circumference 823 and the inner circle 822 which follow the length of the port segment. In this example, the attachment projections 820 are truncated pyramids.

Figure 20:
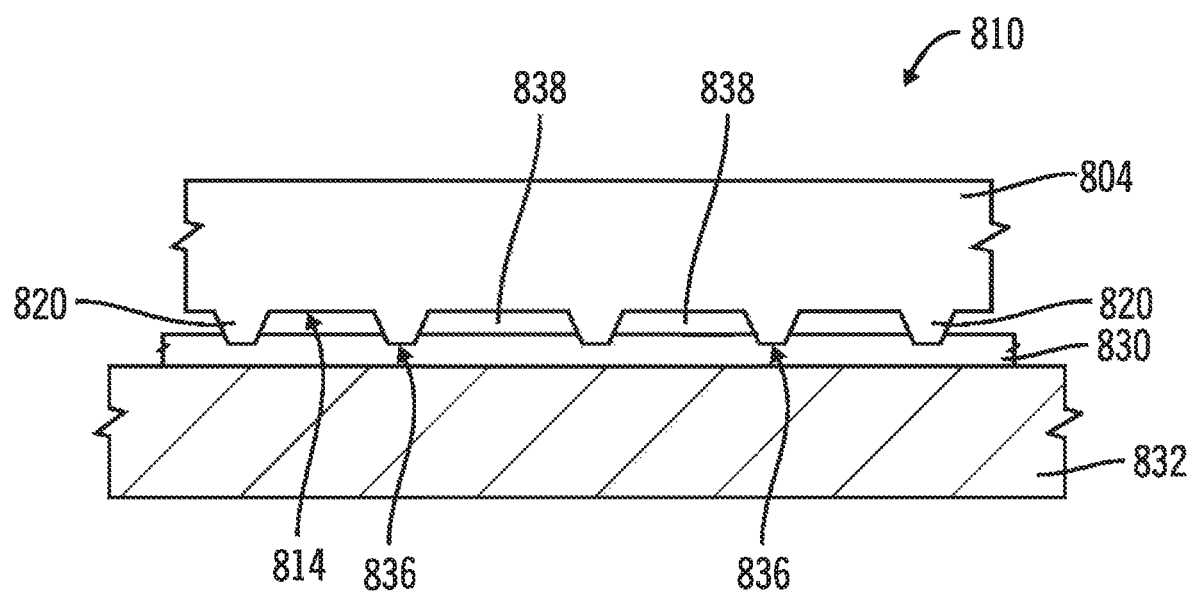

FIG. 20 is a section view of the planar deck 804 of the body 810 along the outer circumference through the attachment projections 820. In this example, the body 810 is plastically welded to a patch 830, which is attached to the skin 832 of a patient. The attachment projections 820 are deformed from the truncated pyramid to a flattened, rounded shape from welding the attachment projections 820 to the patch 830 at each fixation point 836. In this example, the tips of the attachment projections 820 are welded into the patch 830, i.e., the tips of the attachment projections rest below the surface of the patch at the fixation points 836 where the attachment projections 820 join the patch 830. In cross section through adjacent attachment projections 820, the patient face 814 and the patch 830 define a ventilation gap 838 to provide ventilation and air circulation between the planar deck 804 and the patch 830, cooling the skin 832 across the patch 830 from the ventilation gap 838.

Those skilled in the art will appreciate that the design of the patch 830 can be selected as desired for a particular application. The patch can be made of any biocompatible material with biocompatible adhesive operable to hold the weight of the injection device to the skin for a predetermined number of days. The patch design also needs to account for ventilation and circulation between the patch and the skin. In one example, the patch is a continuous sheet of adhesive material. In another example, the patch is a mesh sheet of adhesive material including perforations. In yet another example, the patch is a continuous sheet of adhesive material with holes cut into the continuous sheet. The holes can align with features of the body of the injection device, such as the cutouts, as desired. The holes can optionally be the same size as the cutouts. In yet another example, the patch is a continuous sheet of adhesive material with holes cut into the continuous sheet, and mesh applied across the holes. In yet another example, the patch can be made of a transparent material to allow the condition of the skin around and below the injection device to be monitored. In one example, adhesive patches are constructed of pressure sensitive acrylic-based adhesives with non-woven polyester backings.

Those skilled in the art will further appreciate that the design of the body of the injection device can be selected as desired for a particular application. In one example, the number and position of the cutouts in the planar deck can be selected to provide ventilation to the skin while maintaining sufficient rigidity for the planar deck. In another example, the number and position of the cutouts can be selected to allow observation of the condition of the skin around and below the injection device. In yet another example, the body of the injection device can be made of a transparent material to allow the condition of the skin around and below the injection device to be monitored. This is particularly useful when the patch includes holes or is made from a transparent material. Exemplary materials for the body of the injection device include polycarbonate, acrylic, or the like. In one embodiment, one or more optical elements can be molded into the body of the injection device to magnify the area or areas of interest.

FIGS. 21-24 are various embodiments of septums for use in an injection device. The septums can be disposed in the injection device channels. In one embodiment, the septum is self sealing to block fluid flow through the septum after a needle has been put through the septum then removed, preventing fluid flow through the port connected to the channel.

Figure 21:
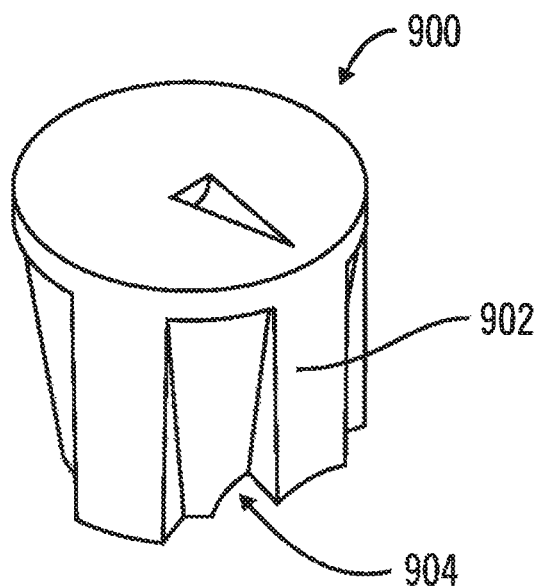
FIG. 21 is a perspective view of one embodiment of an introducer septum for use in an injection device made in accordance with the invention.

FIG. 21 is a perspective view of one embodiment of an introducer septum for use in an injection device made in accordance with the invention. In this embodiment, the introducer septum is irregular-shaped, i.e., the introducer septum has an irregular shape. The introducer septum 900 includes a number of legs 902 to secure the introducer septum 900 in the introducer channel.

Figure 22:
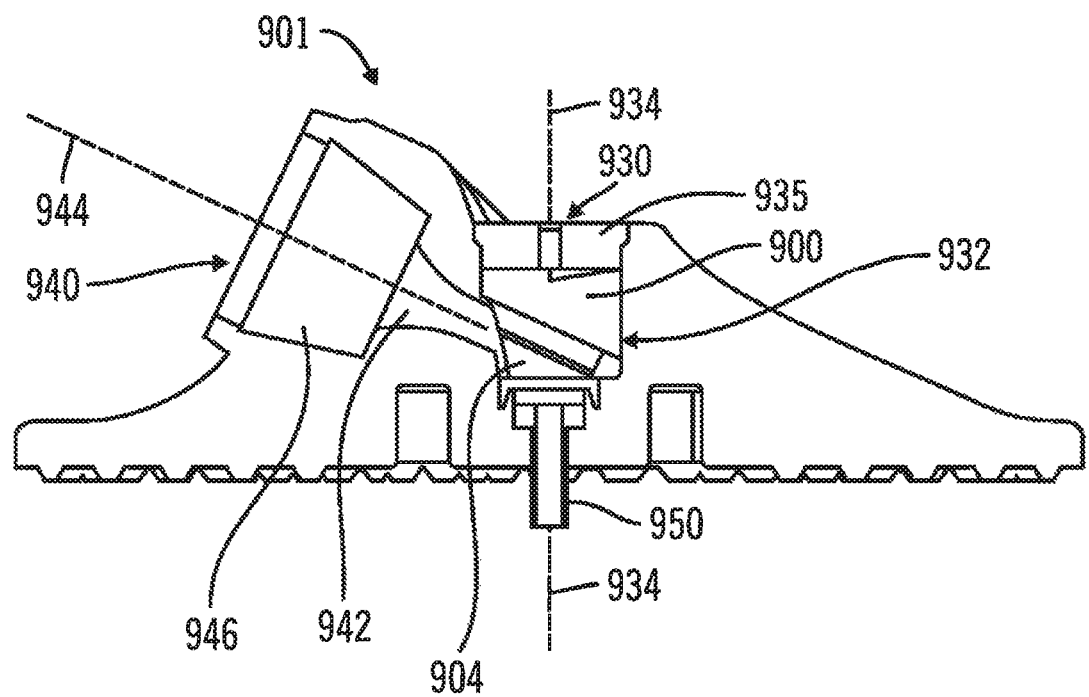
FIG. 22 is a section view of an injection device made in accordance with the invention including the introducer septum of FIG. 21.

FIG. 22 is a section view of an injection device made in accordance with the invention including the introducer septum of FIG. 20. The section bisects the introducer port 930 and the injection port 940, and includes the introducer axis 934 and injection axis 944. The delivery tube 950 is operably connected to the introducer port 930 and defines an introducer axis 934, the delivery tube 950 being in fluid communication with the injection port 940. The introducer port 930 includes an introducer channel 932, with an introducer port cover 935 and the introducer septum 900 disposed in the introducer channel 932. The introducer septum 900 is secured in the introducer channel 932 of the injection device 901 by legs 902. The injection port 940 includes an injection channel 942 defining an injection axis 944 with an injection septum 946 disposed in the injection channel 942. The injection channel 942 is in fluid communication with the delivery tube 950 through a septum connection channel 904 in the introducer septum 900. The introducer septum 900 both connects the injection port 940 to the delivery tube 950 and fills extra space within the introducer channel 932 to avoid an unnecessary amount of therapeutic agent from collecting in the introducer channel 932.

Figure 23:
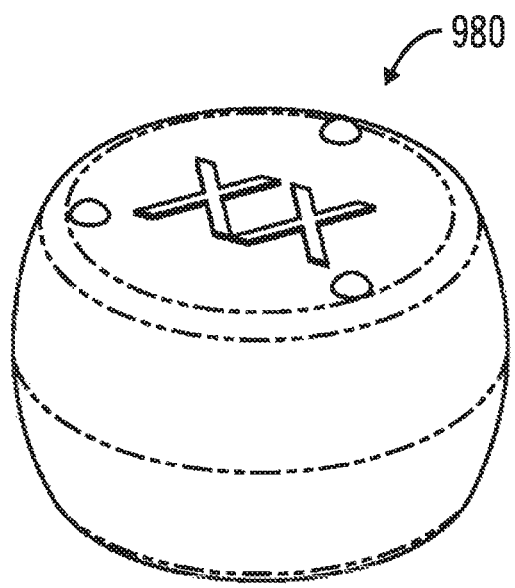
FIG. 23 is a perspective view of one embodiment of a septum for use in an injection device made in accordance with the invention.

FIG. 23 is a perspective view of one embodiment of a septum for use in an injection device made in accordance with the invention. In this embodiment, the septum is barrel-shaped. The barrel-shape septum 980 can be used as an introducer septum or an injection septum as desired for a particular application.

Figure 24A:
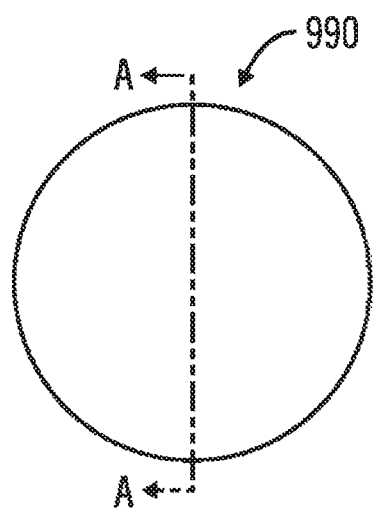
FIGS. 24A & 24B are top side and section views, respectively, of one embodiment of a septum for use in an injection device made in accordance with the invention.
Figure 24B:
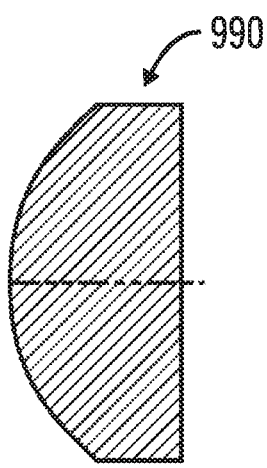

FIGS. 24A & 24B are top side and A-A section views, respectively, of one embodiment of a septum for use in an injection device made in accordance with the invention. In this embodiment, the septum is dome-shaped. The dome septum 990 can be used as an introducer septum or an injection septum as desired for a particular application.

It is important to note that FIGS. 1-24 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. An injection device for delivering a therapeutic agent to a patient, the injection device comprising:
a body having a patient face and a port face opposite the patient face, the port face having an introducer port including an introducer channel and an injection port including an injection channel, the injection channel defining a single injection axis, a cross channel connecting the introducer channel to the injection channel, the introducer channel being in fluid communication with the injection channel through the cross channel;
a delivery tube for subcutaneous delivery of the therapeutic agent to the patient, the delivery tube projecting from and being generally perpendicular to the patient face, the delivery tube defining a single introducer axis and being in fluid communication with the injection port;
wherein the injection axis is parallel to and does not intersect the introducer axis;
a patch attached to the patient face and operable to adhesively attach to the patient; and
a pop-up indicator disposed in the introducer channel, the pop-up indicator having a normal state when pressure in the introducer channel is normal and an alarm state when pressure in the introducer channel exceeds a predetermined value.

2. The injection device of claim 1, wherein the pop-up indicator includes a self-closing port operable to receive a needle of a needle hub assembly.

3. The injection device of claim 1, wherein the pop-up indicator has a membrane selected from the group consisting of a folded membrane, an accordion membrane, and a deformable membrane.

4. The injection device of claim 1, the cross channel defining a single cross channel axis, wherein the cross channel axis intersects both the injection axis and the introducer axis.

5. The injection device of claim 4, wherein the cross channel axis is substantially perpendicular to both the injection axis and the introducer axis.

6. The injection device of claim 1, wherein the cross channel connects an end of the injection channel that is distal to the injection port and an end of the introducer channel that is proximate to the introducer port.

7. An injection device for delivering a therapeutic agent to a patient, the injection device comprising:
a body having a patient face and a port face opposite the patient face, the port face having an introducer port including an introducer channel and an injection port including an injection channel, the injection channel defining a single injection axis, a cross channel connecting the introducer channel to the injection channel, the introducer channel being in fluid communication with the injection channel through the cross channel;
a delivery tube for subcutaneous delivery of the therapeutic agent to the patient, the delivery tube projecting from and being generally perpendicular to the patient face, the delivery tube defining a single introducer axis and being in fluid communication with the injection port;
wherein the injection axis is parallel to and does not intersect the introducer axis;
a patch attached to the patient face and operable to adhesively attach to the patient; and
wherein the body has a first body portion including the port face and a second body portion including the patient face, the first body portion and the second body portion being rotatably connected with a flange, the first body portion and the second body portion being independently rotatable about the introducer axis.

8. The injection device of claim 7, the cross channel defining a single cross channel axis, wherein the cross channel axis intersects both the injection axis and the introducer axis.

9. The injection device of claim 8, wherein the cross channel axis is substantially perpendicular to both the injection axis and the introducer axis.

10. The injection device of claim 7, wherein the cross channel connects an end of the injection channel that is distal to the injection port and an end of the introducer channel that is proximate to the introducer port.

11. An injection device for delivering a therapeutic agent to a patient, the injection device comprising:
a body having a patient face and a port face opposite the patient face, the port face having an introducer port including an introducer channel and an injection port including an injection channel, the injection channel defining a single injection axis, a cross channel connecting the introducer channel to the injection channel, the introducer channel being in fluid communication with the injection channel through the cross channel;
a delivery tube for subcutaneous delivery of the therapeutic agent to the patient, the delivery tube projecting from and being generally perpendicular to the patient face, the delivery tube defining a single introducer axis and being in fluid communication with the injection port;
wherein the injection axis is parallel to and does not intersect the introducer axis;
a patch attached to the patient face and operable to adhesively attach to the patient; and
an injection septum.

12. The injection device of claim 11, the cross channel defining a single cross channel axis, wherein the cross channel axis intersects both the injection axis and the introducer axis.

13. The injection device of claim 12, wherein the cross channel axis is substantially perpendicular to both the injection axis and the introducer axis.

14. The injection device of claim 11, wherein the cross channel connects an end of the injection channel that is distal to the injection port and an end of the introducer channel that is proximate to the introducer port.

15. An injection device for delivering a therapeutic agent to a patient, the injection device comprising:
a body having a patient face and a port face opposite the patient face, the port face having an introducer port including an introducer channel and an injection port including an injection channel, a cross channel connecting the introducer channel to the injection channel, wherein the cross channel connects an end of the injection channel that is distal to the injection port to an end of the introducer channel that is proximate to the introducer port, the introducer channel being in fluid communication with the injection channel through the cross channel, the cross channel defining a single cross channel axis and the injection channel defining a single injection axis;
a delivery tube for subcutaneous delivery of the therapeutic agent to the patient, the delivery tube projecting from and being generally perpendicular to the patient face, the delivery tube defining a single introducer axis and being in fluid communication with the injection port;
a patch attached to the patient face and operable to adhesively attach to the patient; and
an injection adapter assembly connectable to the injection port, the injection adapter assembly being operable to receive a needleless pen injector;
wherein the injection axis is parallel to and does not intersect the introducer axis; and
wherein the cross channel axis is substantially perpendicular to and intersects both the injection axis and the introducer axis.

* * * * *